United States Patent
Tsunoda et al.

(10) Patent No.: US 8,735,361 B2
(45) Date of Patent: May 27, 2014

(54) C1ORF59 PEPTIDES AND VACCINES INCLUDING THE SAME

(75) Inventors: Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 13/141,389

(22) PCT Filed: Dec. 17, 2009

(86) PCT No.: PCT/JP2009/006944
§ 371 (c)(1),
(2), (4) Date: Sep. 8, 2011

(87) PCT Pub. No.: WO2010/073551
PCT Pub. Date: Jul. 1, 2010

(65) Prior Publication Data
US 2012/0003253 A1    Jan. 5, 2012

Related U.S. Application Data

(60) Provisional application No. 61/145,912, filed on Jan. 20, 2009.

(30) Foreign Application Priority Data

Dec. 24, 2008   (JP) ................................. 2008-327358

(51) Int. Cl.
*A61K 38/08* (2006.01)
*A61K 48/00* (2006.01)
*C12N 15/11* (2006.01)

(52) U.S. Cl.
USPC ......... 514/21.6; 530/327; 530/328; 536/23.1; 514/44 R

(58) Field of Classification Search
None
See application file for complete search history.

(56) References Cited

U.S. PATENT DOCUMENTS

| | | | |
|---|---|---|---|
| 2006/0216301 A1 | 9/2006 | Tahara et al. | |
| 2007/0083334 A1* | 4/2007 | Mintz et al. | 702/19 |

FOREIGN PATENT DOCUMENTS

| | | |
|---|---|---|
| CN | 101024842 A | 8/2007 |
| JP | 2006-052216 A | 2/2006 |
| TW | 2005/02247 | 1/2005 |
| WO | 03/063770 A2 | 8/2003 |
| WO | WO 2004/024766 A1 | 3/2004 |
| WO | 2006/090810 A2 | 8/2006 |
| WO | 2008/102557 | 8/2008 |
| WO | WO 2008/118258 A2 * | 10/2008 |
| WO | WO 2010/073551 A1 | 7/2010 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Tokuriki et al., 2009, Curr. Opin. Struc. Biol. 19:596-604.*
Shen et al., 2012, Cancer Immunol. Immunother., Epub ahead of print, pp. 1-11.*
Bocchia et al., 2000, Haematologia 85:1172-1206.*
Strausberg, et al., NCBI Accession No. AAH12198.1, retrieved from http://www.ncbi.nlm.nih.gov/protein/15082589, 2 pages (Jul. 15, 2006).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Boon T., "Tumor Antigens Recognized by Cytolytic T Lymphocytes: Present Perspectives for Specific Immunotherapy," *Int J Cancer*, vol. 54(2), pp. 177-180 (May 8, 1993).
Boon T., et al., "Human Tumor Antigens Recognized by T Lymphocytes," *J Exp Med.*, vol. 183(3), pp. 725-729 (Mar. 1, 1996).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Coulie, et al., "Cytolytic T-cell responses of cancer patients vaccinated with a MAGE antigen," *Immunol Rev.*, vol. 188, pp. 33-42 (Oct. 2002).
Fujie, et al., "A *MAGE*-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Kikuchi, et al., "Identification of a SART-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

(Continued)

*Primary Examiner* — Elizabeth C Kemmerer
(74) *Attorney, Agent, or Firm* — Kilpatrick Townsend & Stockton LLP

(57) ABSTRACT

The present invention provides isolated peptides having the amino acid sequence of SEQ ID NO: 43 or immunologically active fragments thereof, which bind to HLA antigen and have cytotoxic T lymphocyte (CTL) inducibility. The present invention further provides peptides which include one, two, or several amino acid insertions, substitution or addition to the aforementioned peptides or fragments, but still have the cytotoxic T cell inducibility. Further provided are nucleic acids encoding any of these aforementioned peptides as well as pharmaceutical agents and compositions including any of the aforementioned peptides or nucleic acids. The peptides, nucleic acids, pharmaceutical agents and compositions of this invention may be used for treating cancer or tumor.

9 Claims, 8 Drawing Sheets

(56) References Cited

OTHER PUBLICATIONS

Kirino, et al., "The mouse homolog of HEN1 is a potential methylase for Piwi-interacting RNAs," *RNA*, vol. 13(9), pp. 1397-1401 (Sep 2007, Epub Jul. 24, 2007).

Oiso, et al., "A Newly Identified *MAGE*-3-Derived Epitope Recognized by HLA-A24-Restricted Cytotoxic T Lymphocytes," *Int J Cancer*, vol. 81(3), pp. 387-394 (May 5, 1999).

Rosenberg, et al., "Cancer immunotherapy: moving beyond current vaccines," *Nat Med.*, vol. 10(9), pp. 909-915 (Sep. 2004).

Saito, et al., "Pimet, the *Drosophila*homolog of HEN1, mediates 2'-O-methylation of Piwi-interacting RNAs at their 3' ends," *Genes Dev.*, vol. 21(13), pp. 1603-1608 (Jul. 1, 2007).

Strausberg, et al., "Generation and initial analysis of more than 15,000 full-length human and mouse cDNA sequences," *Proc Natl Acad Sci USA*, vol. 99(26), pp. 16899-16903 (Dec. 24, 2002, Epub Dec. 11, 2002).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Van Der Burg, et al., "Immunogenicity of Peptides Bound to MHC Class 1 Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

Database Genbank, NP 001096062, 1 page (Aug. 29, 2008).

NCBI Accession No. GDS823, 2 pages (Apr. 12, 2004, Search: Feb. 3, 2010).

NCBI Accession No. GDS1761, 2 pages (Nov. 24, 2004, Search: Feb. 3, 2010).

NCBI Accession No. GDS2902, 2 pages (Aug. 23, 2007, Search: Feb. 3, 2010).

Adams, et al. "Prediction of binding to MHC class I molecules," *J Immunol Methods*, vol. 185(2), pp. 181-190 (Sep. 25, 1995).

Dionne, et al., "Functional characterization of CTL against gp100 altered peptide ligands," *Cancer Immunol Immunother.*, vol. 52(4), pp. 199-206 (Apr 2003, Epub Feb. 18, 2003).

Dionne, et al., "Her-2/*neu*altered peptide ligand-induced CTL responses: implications for peptides with increased HLA affinity and T-cell-receptor interaction," *Cancer Immunol. Immunother.*, vol. 53(4), pp. 307-314 (Apr. 2004, Epub Nov. 5, 2003).

Falk, et al., "Allele-specific motifs revealed by sequencing of self-peptides eluted from MHC molecules," *Nature*, vol. 351(6324), pp. 290-296 (May 23, 1991).

Hoffman, et al., "The Ability of Variant Peptides to Reverse the Nonresponsiveness of T Lymphocytes to the Wild-Type Sequence p. $53_{264-272}$Epitope," *J Immunol.*, vol. 168(3), pp. 1338-1347 (Feb. 1, 2002).

Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Pinilla-Ibarz, et al., "Synthetic peptide analogs derived from bcr/abl fusion proteins and the induction of heteroclitic human T-cell responses," *Haematologica*, vol. 90(10), pp. 1324-1332 (Oct. 2005).

Rammensee, et al., "MHC ligands and peptide motifs: first listing," *Immunogenetics*, vol. 41(4), pp. 178-228 (1995).

Schueler, et al., "Structure-based prediction of binding peptides to MHC class I molecules: Application to a broad range of MHC alleles," *Protein Sci.*, vol. 9(9), pp. 1838-1846 (Sep. 2000).

Suda, et al., "Identification of human leukocyte antigen-A24-restricted epitope peptides derived from gene products upregulated in lung and esophageal cancers as novel targets for immunotherapy," *Cancer Sci.*vol. 98(11), pp. 1803-1808 (Sep. 2007).

Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).

Zhu, et al., Improving MHC binding peptide prediction by incorporating binding data of auxiliary MHC molecules, *Bioinformatics*, vol. 22(13), pp. 1648-1655 (Jul. 1, 2006, Epub Apr. 13, 2006).

Lamesch, et al., GenBank Accession No. NM_144584.2, 2 pages, dated Aug. 29, 2008.

Roitt et al., Immunology, 2000, pp. 159-163. Corresponding English document of Roitt et al., Immunology, 2000, pp. 159-163.

Marsh et al., *The HLA FactsBook*, Academic Press, pp. 105 (2000).

Marsh et al., *The HLA FactsBook*, Academic Press, pp. 121 (2000).

Komori et al., "Identification of HLA-A2- or HLA-A24-Restricted CTL Epitopes Possibly Useful for Glypican-3-Specific Immunotherapy of Hepatocellular Carcinoma", *Clin. Cancer Res.* vol. 12, No. 9, pp. 2689-2697 (2006).

* cited by examiner

Fig. 4
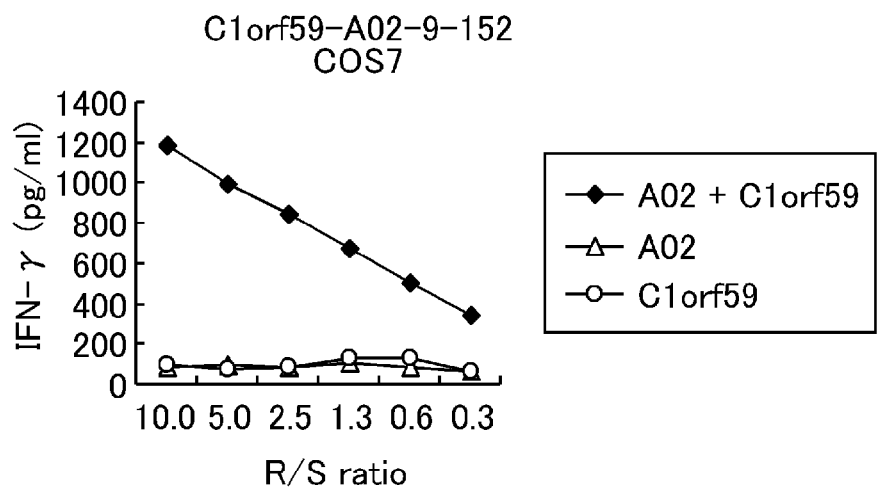
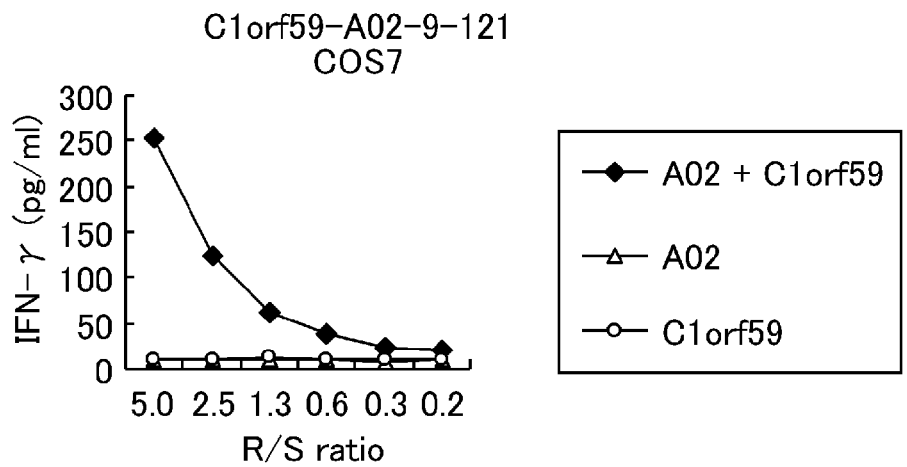
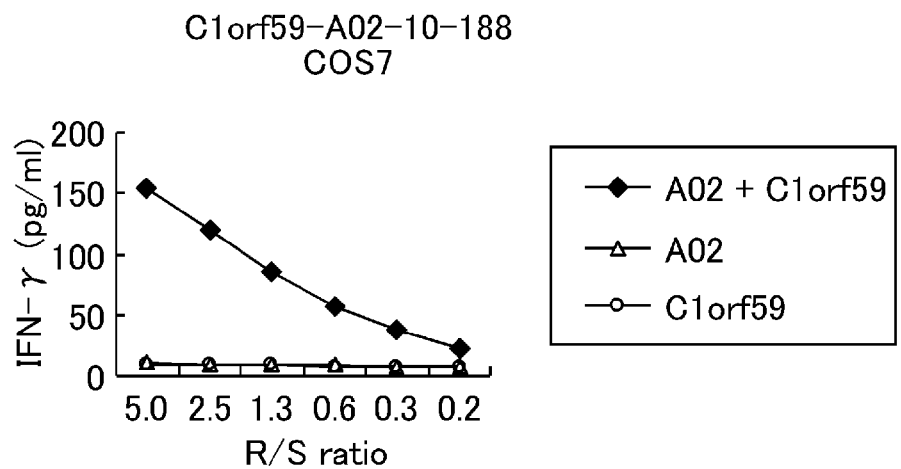

Fig. 8
a  C1orf59-A24-9-221 clone #5 L.D. #103 COS7
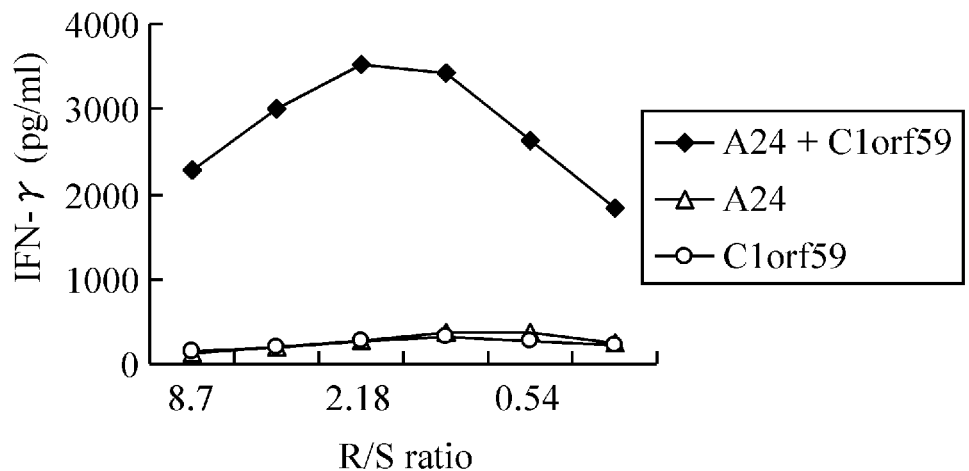
b  C1orf59-A24-9-221 clone #5 L.D. #248 COS7
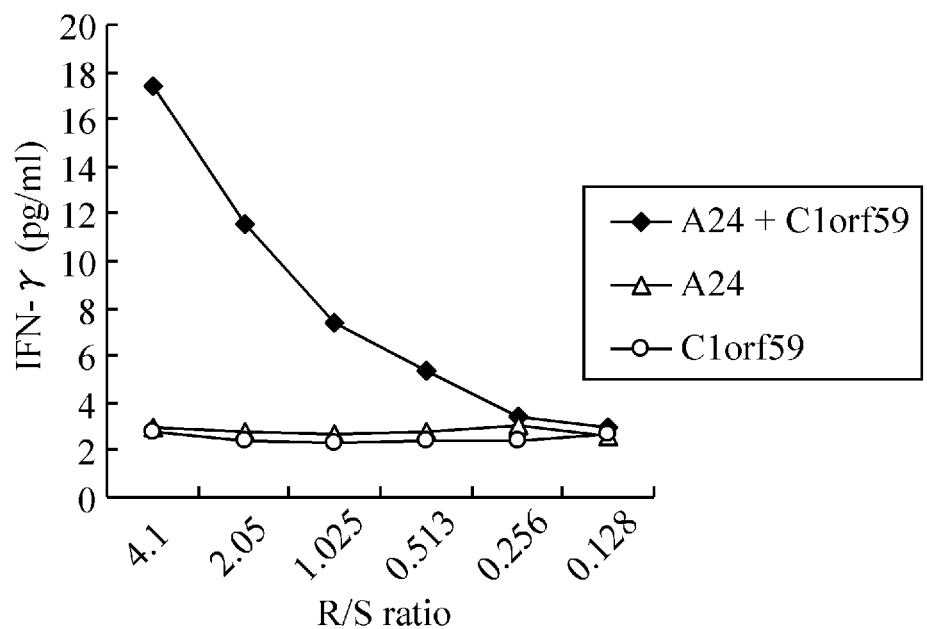

C1ORF59 PEPTIDES AND VACCINES INCLUDING THE SAME

The present application is a U.S. National Stage Application of PCT/JP2009/006944, filed Dec. 17, 2009, which claims the benefit of Japanese Patent Application No. 2008-327358, filed on Dec. 24, 2008, and U.S. Provisional Applications No. 61/145,912, filed on Jan. 20, 2009, the entire contents of which are incorporated by reference herein in their entirety.

TECHNICAL FIELD

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8 positive cytotoxic T lymphocytes (CTLs) recognize epitope peptides derived from the tumor-associated antigens (TAAs) on major histocompatibility complex (MHC) class I molecule, and then kill the tumor cells. Since the discovery of the melanoma antigen (MAGE) family as the first example of TAAs, many other TAAs have been discovered primarily through immunological approaches (NPL 1: Boon T, Int J Cancer 1993 May 8, 54(2): 177-80; NPL 2: Boon T & van der Bruggen P, J Exp Med 1996 Mar. 1, 183(3): 725-9). Some of these TAAs are currently undergoing clinical development as immunotherapeutic targets.

Identification of new TAAs capable of inducing potent and specific anti-tumor immune responses, warrants further development of clinical application of peptide vaccination strategies for various types of cancer (NPL 3: Harris C C, J Natl Cancer Inst 1996 Oct. 16, 88(20): 1442-55; NPL 4: Butterfield L H et al., Cancer Res 1999 Jul. 1, 59(13): 3134-42; NPL 5: Vissers J L et al., Cancer Res 1999 Nov. 1, 59(21): 5554-9; NPL 6: van der Burg S H et al., J Immunol 1996 May 1, 156(9): 3308-14; NPL 7: Tanaka F et al., Cancer Res 1997 Oct. 15, 57(20): 4465-8; NPL 8: Fujie T et al., Int J Cancer 1999 Jan. 18, 80(2): 169-72; NPL 9: Kikuchi M et al., Int J Cancer 1999 May 5, 81(3): 459-66; NPL 10: Oiso M et al., Int J Cancer 1999 May 5, 81(3): 387-94). To date, there have been several clinical reports of trials using these tumor-associated antigen derived peptides (NPL 11: Belli F et al., J Clin Oncol 2002 Oct. 15, 20(20): 4169-80; NPL 12: Coulie P G et al., Immunol Rev 2002 October, 188: 33-42; NPL 13: Rosenberg S A et al., Nat Med 2004 September, 10(9): 909-15).

Chromosome 1 open reading frame 59 (C1orf59) has been identified through cDNA library screening by Mammalian Gene Collection (MGC) (NPL 14: MGC Program Team, Proc Natl Acad Sci USA. 2002 Dec. 24; 99(26):16899-903). However, it has not been confirmed whether C1orf59 might be used as a target for cancer immunotherapy against patients with tumors.

CITATION LIST

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] MGC Program Team, Proc Natl Acad Sci USA. 2002 Dec. 24; 99(26):16899-903

SUMMARY OF INVENTION

The present invention is based in part on the discovery of suitable targets of immunotherapy. Because TAAs are generally perceived for the immune system as "self" and therefore often have no immunogenicity, the discovery of appropriate targets is of extreme importance. As noted above, C1orf59 (SEQ ID NO: 43 encoded by the gene of GenBank Accession No. NM_144584 (SEQ ID NO: 42)) has been identified as up-regulated in tissues of cancers, such as bladder cancer, breast cancer, cervical cancer, colorectal cancer, esophagus cancer, non-small cell lung cancer (NSCLC), osteosarcoma, ovarian cancer, pancreatic cancer, prostate cancer and small cell lung cancer (SCLC). Thus, C1orf59 is a candidate target of immunotherapy.

The present invention is based, at least in part, on the identification of specific epitope peptides of C1orf59, which possess the ability to induce cytotoxic T lymphocytes (CTLs) specific to C1orf59. As discussed in detail below, peripheral blood mononuclear cells (PBMCs) obtained from a healthy donor were stimulated using HLA-A*0201 or A*2402 binding candidate peptides derived from C1orf59. CTL lines with specific cytotoxicity against HLA-A02 or A24 positive target cells pulsed with each of candidate peptides were then established. These results demonstrate that these peptides are HLA-A02 or A24 restricted epitope peptides that can induce potent and specific immune responses against cells expressing C1orf59. These results demonstrate that C1orf59 is strongly immunogenic and the epitopes thereof are effective targets for tumor immunotherapy.

Accordingly, it is an object of the present invention to provide isolated peptides derived from C1orf59 (SEQ ID NO: 43) or immunologically active fragments thereof that bind to HLA antigens. The present peptides are expected to have CTL inducibility. They can be used to induce CTL ex vivo or can be administered to a subject for inducing immune responses against cancers such as bladder cancer, breast cancer, cervical cancer, colorectal cancer, esophagus cancer, NSCLC, osteosarcoma, ovarian cancer, pancreatic cancer, prostate cancer and SCLC. Preferably, the peptides are nonapeptides or decapeptides, and typically, consist of the amino acid sequence selected from the group of SEQ ID NOs: 1, 3, 4, 7, 9, 13, 15, 17, 20, 26, 32, 34, 40 and 41, show strong CTL inducibility.

The present invention contemplates modified peptides, having an amino acid sequence of SEQ ID NOs: 1, 3, 4, 7, 9, 13, 15, 17, 20, 26, 32, 34, 40 and 41 wherein one, two or more amino acid(s) is/are substituted or added, so long as the modified peptides retain the original CTL inducibility.

Further, the present invention provides isolated polynucleotides encoding any of the peptides of the present invention. These polynucleotides can be used for inducing antigen-expressing cells (APCs) with CTL inducibility or can be administered to a subject for inducing immune responses against cancers as well as the present peptides.

When administered to a subject, the present peptides are presented on the surface of APCs and then induce CTLs targeting the respective peptides. Therefore, it is an aspect of the present invention to provide agents including any peptides or polynucleotides of the present invention for inducing CTL. Furthermore, agents including any of the peptides or polynucleotides can be used for treating and/or for the prophylaxis of cancers, such as bladder cancer, breast cancer, cervical cancer, colorectal cancer, esophagus cancer, NSCLC, osteosarcoma, ovarian cancer, pancreatic cancer, prostate cancer and SCLC, and/or for preventing postoperative recurrence thereof. Thus, it is yet another object of the present invention to provide pharmaceutical agents for treating and/or for the prophylaxis of cancers, and/or for preventing postoperative recurrence thereof, which include any of the peptides or polynucleotides of the present invention. Instead of or in addition to the present peptides or polynucleotides, the present agents or pharmaceutical agents may include, as the active ingredients, APCs or exosomes which present any of the present peptides.

The peptides or polynucleotides of the present invention may be used to induce APCs which present on its surface a complex of an HLA antigen and the present peptide, for example, by contacting APCs derived from a subject with the present peptide or introducing a polynucleotide encoding the present peptide into APCs. Such APCs have high CTL inducibility against the target peptides and are useful for cancer immunotherapy. Therefore, it is another object of the present invention to provide methods for inducing APCs with CTL inducibility as well as APCs obtained by the methods.

It is a further object of the present invention to provide a method for inducing CTL, which includes the step of co-culturing CD8-positive cells with APCs or exosomes presenting a peptide of the present invention on its surface or the step of introducing a gene that includes a polynucleotide encoding a T cell receptor (TCR) subunit binding to the present peptide. The CTLs obtainable by the present methods also find use in treating and/or preventing cancers in which C1orf59 is overexpressed, such as bladder cancer, breast cancer, cervical cancer, colorectal cancer, esophagus cancer, NSCLC, osteosarcoma, ovarian cancer, pancreatic cancer, prostate cancer and SCLC. Therefore, it is another object of the present invention to provide CTLs obtainable by the present methods.

Moreover, a further object of the present invention is to provide methods for inducing immune response against cancers, which methods include the step of administering agents or compositions containing C1orf59 or immunologically active fragments thereof, polynucleotides encoding C1orf59 or the fragments thereof, or exosomes or APCs presenting C1orf59 or the fragments thereof.

The present invention may be applied to any diseases related to C1orf59 overexpression including cancer, such as bladder cancer, breast cancer, cervical cancer, colorectal cancer, esophagus cancer, NSCLC, osteosarcoma, ovarian cancer, pancreatic cancer, prostate cancer and SCLC.

It is to be understood that both the foregoing summary of the invention and the following detailed description are of exemplified embodiments, and not restrictive of the invention or other alternate embodiments of the invention.

BRIEF DESCRIPTION OF DRAWINGS

Various aspects and applications of the present invention will become apparent to the skilled artisan upon consideration of the brief description of the figures, and the detailed description of the present invention and its preferred embodiments which follows.

FIG. 4 includes a series of line graphs (a)-(c) depicting specific CTL activity against target cells that exogenously express C1orf59 and HLA-A*0201. COS7 cells transfected with HLA-A*0201 or with the full length C1orf59 gene were prepared as control. The CTL lines established with C1orf59-A02-9-152 (SEQ ID NO: 3) (a), C1orf59-A02-9-121 (SEQ ID NO: 4) (b) and C1orf59-A02-10-188 (SEQ ID NO: 15) (c)

showed specific CTL activity against COS7 cells transfected with both C1orf59 and HLA-A*0201 (black lozenge). In contrast, no significant specific CTL activity was detected against target cells expressing either HLA-A*0201 (triangle) or C1orf59 (circle).

Figure 5:
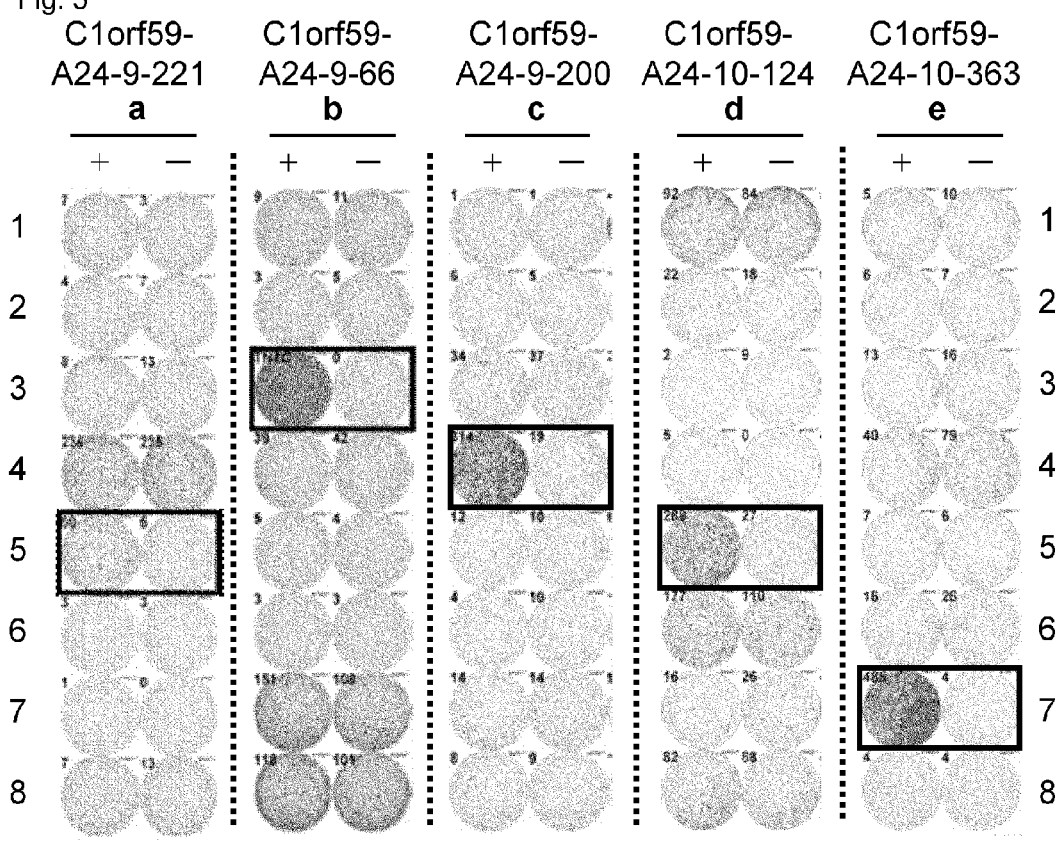

FIG. 5 depicts photographs showing the results of IFN-gamma ELISPOT assay on CTLs that were induced with peptides derived from C1orf59. The CTLs in the well number #5 stimulated with C1orf59-A24-9-221 (SEQ ID NO: 26) (a), #3 with C1orf59-A24-9-66 (SEQ ID NO: 32) (b), #4 with C1orf59-A24-9-200 (SEQ ID NO: 34) (c), #5 with C1orf59-A24-10-124 (SEQ ID NO: 40) (d) and #7 with C1orf59-A24-10-363 (SEQ ID NO: 41) (e) showed potent IFN-gamma production compared with the control, respectively. The square on the well of these pictures indicates that the cells from corresponding well were expanded to establish CTL lines. In the figures, "+" indicates that the cells in the wells were pulsed with appropriate peptides, and "−" indicates that the cells had not been pulsed with the peptides.

Figure 6:
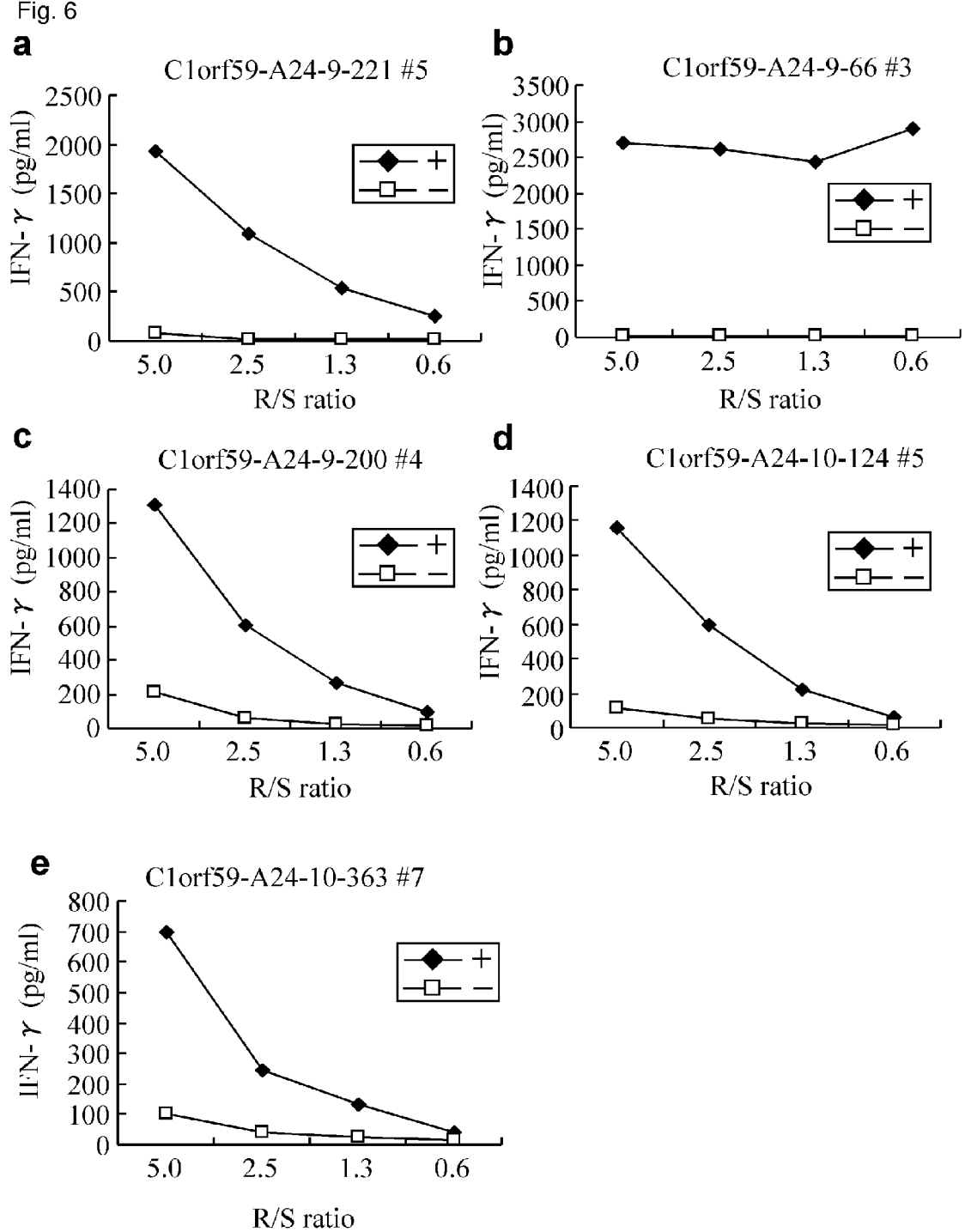

FIG. 6 depicts line graphs showing the IFN-gamma production of CTL lines stimulated with C1orf59-A24-9-221 (SEQ ID NO: 26) (a), C1orf59-A24-9-66 (SEQ ID NO: 32) (b), C1orf59-A24-9-200 (SEQ ID NO: 34) (c), C1orf59-A24-10-124 (SEQ ID NO: 40) (d) and C1orf59-A24-10-363 (SEQ ID NO: 41) (e) with ELISA. It demonstrated that CTL lines established by stimulation with each peptide showed potent IFN-gamma production compared with the control. In the figures, "+" indicates that the cells were pulsed with the appropriate peptide and "−" indicates that the cells had not been pulsed with any peptides.

Figure 7:
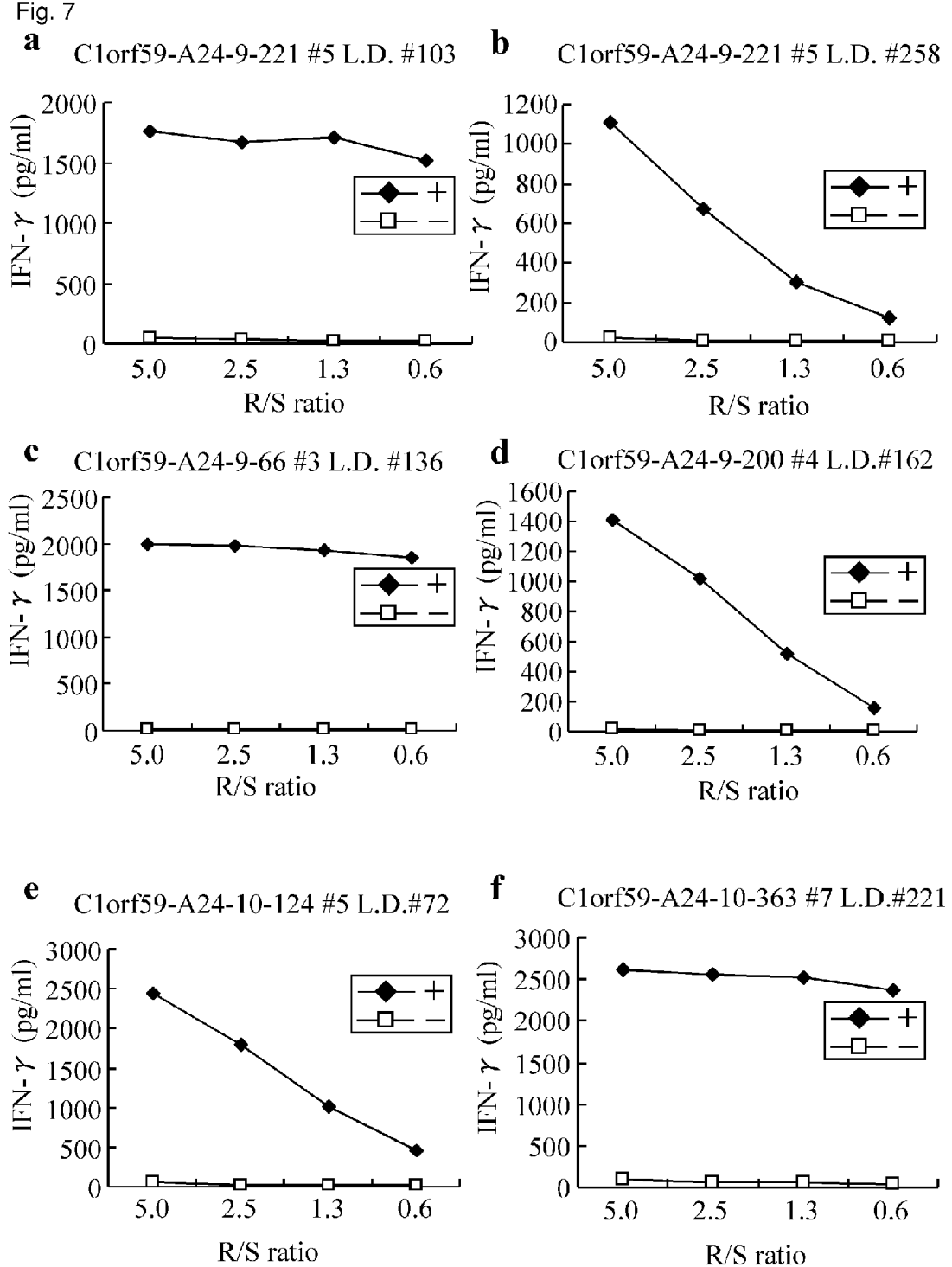

FIG. 7 shows the IFN-gamma production of the CTL clones established by limiting dilution from the CTL lines stimulated with C1orf59-A24-9-221 (SEQ ID NO: 26) (a and b), C1orf59-A24-9-66 (SEQ ID NO: 32) (c), C1orf59-A24-9-200 (SEQ ID NO: 34) (d), C1orf59-A24-10-124 (SEQ ID NO: 40) (e) and C1orf59-A24-10-363 (SEQ ID NO: 41) (f). It demonstrated that the CTL clones established by these peptides showed potent IFN-gamma production compared with the control. In the figures, "+" indicates that the cells were pulsed with SEQ ID NO: 26 (a and b), SEQ ID NO: 32 (c), SEQ ID NO: 34 (d), SEQ ID NO: 40 (e) and SEQ ID NO: 41 (f) and "−" indicates that the cells had not pulsed with any peptides.

FIG. 8 depicts line graphs showing specific CTL activity against the target cells that express C1orf59 and HLA-A*2402. COS7 cells transfected with only HLA-A*2402 or with the full length C1orf59 gene only, were prepared as control. The CTL clones established with C1orf59-A24-9-221 (SEQ ID NO: 26) showed specific CTL activity against COS7 cells transfected with both C1orf59 and HLA-A*2402 (black lozenge). On the other hand, no significant specific CTL activity was detected against target cells expressing either HLA-A*2402 (triangle) or C1orf59 (circle).

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Amino acid can be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are similarly to the amino acids referred to by their commonly accepted single-letter codes.

Unless otherwise defined, the term "cancer" refers to the cancers overexpressing C1orf59 gene, examples of which include, but are not limited to bladder cancer, breast cancer, cervical cancer, colorectal cancer, esophagus cancer, non-small cell lung cancer (NSCLC), osteosarcoma, ovarian cancer, pancreatic cancer, prostate cancer and small cell lung cancer (SCLC)s.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor cells, virus-infected cells) and inducing the death of such cells.

Unless otherwise defined, the terms "HLA-A02" refers to the HLA-A2 type containing the subtypes such as HLA-A0201 or HLA-A0206.

Unless otherwise defined, all technical and scientific terms used herein have the same meaning as commonly understood by one of ordinary skill in the art to which this invention belongs.

II. Peptides

To demonstrate that peptides derived from C1orf59 function as an antigen recognized by CTLs, peptides derived from C1orf59 (SEQ ID NO: 43) were analyzed to determine whether they were antigen epitopes restricted by HLA-A02 or A24 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A02 binding peptides derived from C1orf59 were identified based on their binding affinities to HLA-A02. The following peptides are the candidate peptides:

C1orf59-A02-9-261 (SEQ ID NO: 1),
C1orf59-A02-9-333 (SEQ ID NO: 2),
C1orf59-A02-9-152 (SEQ ID NO: 3),
C1orf59-A02-9-121 (SEQ ID NO: 4),
C1orf59-A02-9-271 (SEQ ID NO: 5),
C1orf59-A02-9-63 (SEQ ID NO: 6),
C1orf59-A02-9-122 (SEQ ID NO: 7),
C1orf59-A02-10-240 (SEQ ID NO: 9),
C1orf59-A02-10-260 (SEQ ID NO: 10),
C1orf59-A02-10-270 (SEQ ID NO: 11),
C1orf59-A02-10-346 (SEQ ID NO: 12),
C1orf59-A02-10-90 (SEQ ID NO: 13),
C1orf59-A02-10-334 (SEQ ID NO: 14),
C1orf59-A02-10-188 (SEQ ID NO: 15),
C1orf59-A02-10-121 (SEQ ID NO: 16),
C1orf59-A02-10-122 (SEQ ID NO: 17),
C1orf59-A02-10-30 (SEQ ID NO: 18),
C1orf59-A02-10-183 (SEQ ID NO: 19),
C1orf59-A02-10-196 (SEQ ID NO: 20),
C1orf59-A02-10-10 (SEQ ID NO: 21),
C1orf59-A02-10-66 (SEQ ID NO: 22),
C1orf59-A02-10-326 (SEQ ID NO: 23), and
C1orf59-A02-10-252 (SEQ ID NO: 24).

After in vitro stimulation of T-cells by dendritic cells (DCs) loaded with these peptides, CTLs were successfully established using each of the following peptides:

C1orf59-A02-9-261 (SEQ ID NO: 1),
C1orf59-A02-9-152 (SEQ ID NO: 3),
C1orf59-A02-9-121 (SEQ ID NO: 4),
C1orf59-A02-9-122 (SEQ ID NO: 7),
C1orf59-A02-10-240 (SEQ ID NO: 9),
C1orf59-A02-10-90 (SEQ ID NO: 13),
C1orf59-A02-10-188 (SEQ ID NO: 15),
C1orf59-A02-10-122 (SEQ ID NO: 17), and
C1orf59-A02-10-196 (SEQ ID NO: 20).

Candidates of HLA-A24 binding peptides derived from C1orf59 were identified based on their binding affinities to HLA-A24. The following peptides are the candidate peptides:

C1orf59-A24-9-385-25 (SEQ ID NO: 25),
C1orf59-A24-9-221-26 (SEQ ID NO: 26),
C1orf59-A24-9-338-27 (SEQ ID NO: 27),
C1orf59-A24-9-339-28 (SEQ ID NO: 28),
C1orf59-A24-9-182-29 (SEQ ID NO: 29),
C1orf59-A24-9-35-30 (SEQ ID NO: 30),
C1orf59-A24-9-253-31 (SEQ ID NO: 31),
C1orf59-A24-9-66-32 (SEQ ID NO: 32),
C1orf59-A24-9-145-33 (SEQ ID NO: 33),
C1orf59-A24-9-200-34 (SEQ ID NO: 34),
C1orf59-A24-9-257-35 (SEQ ID NO: 35),
C1orf59-A24-9-144-36 (SEQ ID NO: 36),
C1orf59-A24-9-151-37 (SEQ ID NO: 37),
C1orf59-A24-9-338-38 (SEQ ID NO: 38),
C1orf59-A24-9-97-39 (SEQ ID NO: 39),
C1orf59-A24-9-124-40 (SEQ ID NO: 40), and
C1orf59-A24-9-363-41 (SEQ ID NO: 41).

After in vitro stimulation of T-cells by dendritic cells (DCs) loaded with these peptides, CTLs were successfully established using each of the following peptides:

C1orf59-A24-9-221-26 (SEQ ID NO: 26),
C1orf59-A24-9-66-32 (SEQ ID NO: 32),
C1orf59-A24-9-200-34 (SEQ ID NO: 34),
C1orf59-A24-9-124-40 (SEQ ID NO: 40), and
C1orf59-A24-9-363-41 (SEQ ID NO: 41).

These established CTLs show potent specific CTL activity against target cells pulsed with respective peptides. These results herein demonstrate that C1orf59 is an antigen recognized by CTL and that the peptides are epitope peptides of C1orf59 restricted by HLA-A02 or A24.

Since the C1orf59 gene is over expressed in cancer cells of such as bladder cancer, breast cancer, cervical cancer, colorectal cancer, esophagus cancer, NSCLC, osteosarcoma, ovarian cancer, pancreatic cancer, prostate cancer and SCLC and not expressed in most normal organs, it is a good target for immunotherapy. Thus, the present invention provides nonapeptides (peptides consisting of nine amino acid residues) and decapeptides (peptides consisting of ten amino acid residues) corresponding to CTL-recognized epitopes of C1orf59. Preferred examples of nonapeptides and decapeptides of the present invention include those peptides consisting of the amino acid sequence selected among SEQ ID NOs: 1, 3, 4, 7, 9, 13, 15, 17, 20, 26, 32, 34, 40 and 41.

Generally, software programs presently available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in the references to Parker K C et al., J Immunol 1994 Jan. 1, 152(1): 163-75; and Kuzushima K et al., Blood 2001, 98(6): 1872-81. The methods for determining binding affinity is described, for example, in; Journal of Immunological Methods, 1995, 185: 181-190; Protein Science, 2000, 9: 1838-1846. Therefore, one can select immunologically active fragments derived from C1orf59, which have high binding affinity with HLA antigens using such software programs. Thus, the present invention encompasses peptides consisting of any immunologically active fragments derived from C1orf59 which bind with HLA antigens identified using such known programs. The peptide of the present invention may be the peptide consisting of the full length of C1orf59.

The peptides of the present invention can be flanked with additional amino acid residues so long as the resulting peptide retains its CTL inducibility. The amino acid residues to be flanked to the present peptides may be composed of any kind of amino acids so long as they do not impair the CTL inducibility of the original peptide. Thus, the present invention encompasses peptides which include the peptides derived from C1orf59 and have binding affinity to HLA antigens. Such peptides are typically less than about 40 amino acids, often less than about 20 amino acids, usually less than about 15 amino acids.

In general, the modification of one, two or more amino acids in a peptide will not influence the function of the peptide, and in some cases will even enhance the desired function of the original protein. In fact, modified peptides (i.e., peptides composed of an amino acid sequence in which one, two or several amino acid residues have been modified (i.e., substituted, deleted, added or inserted as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NOs: 1, 3, 4, 7, 9, 13, 15, 17, 20, 26, 32, 34, 40 and 41, wherein one, two or even more amino acids are added, inserted and/or substituted.

Those skilled in the art recognize that individual additions or substitutions to an amino acid sequence which alters a single amino acid or a small percentage of amino acids tend to result in the conservation of the properties of the original amino acid sequence. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the modified peptide retains the CTL inducibility of the original peptide. Furthermore, modified peptides should not exclude CTL inducible peptides of polymorphic variants, interspecies homologues, and alleles of C1orf59.

To retain the requisite CTL inducibility one can modify (insert, delete, add and/or substitute) a small number (for example, 1, 2 or several) or a small percentage of amino acids. Herein, the term "several" means 5 or fewer amino acids, for example, 4, 3 or fewer. The percentage of amino acids to be modified is preferably 20% or less, more preferably 15% of less, even more preferably 10% or less or 1 to 5%.

Moreover, peptides of the present invention can be inserted, substituted or added with amino acid residues or amino acid residues may be deleted to achieve a higher binding affinity. When used in the context of immunotherapy, the present peptides should be presented on the surface of a cell or exosome, preferably as a complex with an HLA antigen. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. For example, it may be desirable to substitute the second amino acid from the N-terminus substituted with phenylalanine, tyrosine, methionine, or tryptophan, and/or the amino acid at the C-terminus with phenylalanine, leucine, isoleucine, tryptophan, or methionine in order to increase the HLA-A24 binding. Thus, peptides having the amino acid sequences selected from the group consisting of SEQ ID NOs: 26, 32, 34, 40 and 41 wherein the second amino acid from the N-terminus of the amino acid sequence of SEQ ID NOs is substituted with phenylalanine, tyrosine, methionine, or tryptophan, and peptides, and/or wherein the C-terminus of the amino acid sequence of the SEQ ID NOs is substituted with phenylalanine, leucine, isoleucine, tryptophan, or methionine are encompassed by the present invention. On the other hand, peptides possessing high HLA-A02 binding affinity have their second amino acid from the N-terminus substituted with leucine or methionine, and the amino acid at the C-terminus is substituted with valine or leucine. Thus, peptides having the amino acid sequences of SEQ ID NOs: 1, 3, 4, 7, 9, 13, 15, 17 and 20 wherein the second amino acid from the N-terminus is substituted with leucine or methionine, and/or wherein the C-terminus is substituted with valine or leucine are encompassed by the present invention. Substitutions can be introduced not only at the terminal amino acids but also at the position of potential T cell receptor (TCR) recognition of peptides. Several studies have demonstrated that a peptide with amino acid substitutions can be equal to or better than the original, for example CAP1, $p53_{(264-272)}$, $Her-2/neu_{(369-377)}$ or $gp100_{(209-217)}$ (Zaremba et al. Cancer Res. 57, 4570-4577, 1997, T. K. Hoffmann et al. J Immunol. (2002) Feb. 1; 168 (3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the described peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radio-labeled with $^{51}$Cr and such, and cytotoxic activity can be calculated from radioactivity released from the target cells. Alternatively, CTL inducibility can be assessed by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides or decapeptides selected from peptides consisting of the amino acid sequences indicated by SEQ ID NOs: 1, 3, 4, 7, 9, 13, 15, 17, 20, 26, 32, 34, 40 and 41 showed particularly high CTL inducibility as well as high binding affinity to an HLA antigen. Thus, these peptides are exemplified as preferred embodiments of the present invention.

Furthermore, the result of homology analysis showed that those peptides do not have significant homology with peptides derived from any other known human gene products. This lowers the possibility of unknown or undesired immune responses when used for immunotherapy. Therefore, also from this aspect, these peptides find use for eliciting immunity in cancer patients against C1orf59. Thus, the peptides of the present invention, preferably, peptides consisting of the amino acid sequence selected from the group consisting of SEQ ID NOs: 1, 3, 4, 7, 9, 13, 15, 17, 20, 26, 32, 34, 40 and 41.

In addition to the modification of the present peptides discussed above, the described peptides can be further linked to other substances, so long as they retain the CTL inducibility of the original peptide. Exemplary substances include: peptides, lipids, sugar and sugar chains, acetyl groups, natural and synthetic polymers, etc. The present peptides can contain modifications such as glycosylation, side chain oxidation, and/or phosphorylation; so long as the modifications do not destroy the biological activity of the original peptide. These kinds of modifications may confer additional functions (e.g., targeting function, and delivery function) and/or stabilize the peptides.

For example, to increase the in vivo stability of a polypeptide, it is known in the art to introduce D-amino acids, amino acid mimetics or unnatural amino acids; this concept can also be adopted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302). Herein, the peptides of the present invention can also be described as "C1orf59 peptide(s)" or "C1orf59 polypeptide(s)".

III. Preparation of C1orf59 Peptides

The peptides of the invention can be prepared using well known techniques. For example, the peptides can be prepared synthetically, using recombinant DNA technology or chemical synthesis. The peptides of the invention can be synthesized individually or as longer polypeptides composed of two or more peptides. The peptides can then be isolated i.e., purified or isolated so as to be substantially free of other naturally occurring host cell proteins and fragments thereof, or any other chemical substances.

A peptide of the present invention can be obtained through chemical synthesis based on the selected amino acid sequence. Examples of conventional peptide synthesis methods that can be adapted to the synthesis include, but are not limited to:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adapting an in vitro translation system.

IV. Polynucleotides

The present invention also provides a polynucleotide which encodes any of the aforementioned peptides of the present invention. These include polynucleotides derived from the natural occurring C1orf59 gene (GenBank Accession No. NM_144584 (SEQ ID NO: 42)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. Exosomes

The present invention further provides intracellular vesicles called exosomes, which present complexes formed between the peptides of this invention and HLA antigens on their surface. Exosomes can be prepared, for example, by using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

The type of HLA antigens contained in the complexes must match that of the subject requiring treatment and/or prevention. For example, in the Japanese population, HLA-A02 (particularly, A*0201 and also A*0206) and A24 (particularly, A*2402) are prevalent and therefore would be appropriate for treatment of a Japanese patient. The use of the A02 or A24 type that is highly expressed among the Japanese and Caucasian is favorable for obtaining effective results. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion and/or addition of 1, 2, or several amino acids can be performed based on the amino acid sequence of the naturally occurring C1orf59 partial peptide.

When using the A02 type HLA antigen for the exosome of the present invention, the peptides having a sequence of any one of SEQ ID NOs: 1, 3, 4, 7, 9, 13, 15, 17 and, 20 find use. Alternatively, when using the A24 type HLA antigen for the exosome of the present invention, the peptides having a sequence of any one of SEQ ID NOs: 26, 32, 34, 40 and 41 find use.

VI. Antigen-Presenting Cells (APCs)

The present invention also provides isolated APCs that present complexes formed between HLA antigens and the peptides of this invention on its surface. The APCs can be derived from patients who are subjected to treatment and/or prevention, and can be administered as vaccines by themselves or in combination with other drugs including the peptides of this invention, exosomes, or CTLs.

The APCs are not limited to a particular kind of cells and include DCs, Langerhans cells, macrophages, B cells, and activated T cells, which are known to present proteinaceous antigens on their cell surface so as to be recognized by lymphocytes. Since a DC is a representative APC having the strongest CTL inducing action among APCs, DCs find use as the APCs of the present invention.

For example, the APCs of the present invention can be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. Therefore, the APCs of this invention can be obtained by collecting the APCs from the subject after administering the peptides of this invention to the subject. Alternatively, the APCs of this invention can be obtained by contacting APCs collected from a subject with the peptide of this invention.

The APCs of the present invention can be administered alone or in combination with other drugs including the peptides, exosomes or CTLs of this invention to a subject for inducing immune response against cancer in the subject. For example, the ex vivo administration can include steps of:

a: collecting APCs from a first subject,
    b: contacting the APCs of step a, with the peptide and
    c: administering the APCs of step b to a second subject.

The first subject and the second subject can be the same individual, or may be different individuals. The APCs obtained by step b can be administered as a vaccine for treating and/or preventing cancer including bladder cancer, breast cancer, cervical cancer, colorectal cancer, esophagus cancer, NSCLC, osteosarcoma, ovarian cancer, pancreatic cancer, prostate cancer and SCLC.

The present invention also provides a method or process for manufacturing a pharmaceutical composition inducing APCs, wherein the method includes the step of admixing or formulating the peptide of the invention with a pharmaceutically acceptable carrier.

According to an aspect of the present invention, the APCs have a high level of CTL inducibility. In the term of "high level of CTL inducibility", the high level is relative to the level of that by APC contacting with no peptide or peptides which cannot induce the CTL. Such APCs having a high level of CTL inducibility can be prepared by a method which includes the step of transferring a polynucleotide encoding the peptide of this invention to APCs in vitro as well as the method mentioned above. The introduced genes can be in the form of DNAs or RNAs. Examples of methods for introduction include, without particular limitations, various methods conventionally performed in this field, such as lipofection, electroporation, and calcium phosphate method. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VII. Cytotoxic T Lymphocytes (CTLs)

A CTL induced against any of the peptides of the present invention strengthens the immune response targeting cancer cells in vivo and thus can be used as vaccines in a fashion similar to the peptides per se. Thus, the present invention also provides isolated CTLs that are specifically induced or activated by any of the present peptides. Such CTLs can be obtained by (1) administering the peptide(s) of the present invention to a subject, and collecting CTLs from the subject; (2) contacting (stimulating) subject-derived APCs and CD8-positive cells, or peripheral blood mononuclear leukocytes in vitro with the peptide(s) of the present invention and then isolating CTLs; (3) contacting CD8-positive cells or peripheral blood mononuclear leukocytes in vitro with APCs or exosomes presenting a complex of an HLA antigen and the present peptide on its surface and then isolating CTLs; or (4) introducing a gene including a polynucleotide encoding a T cell receptor (TCR) subunit binding to the peptide of this invention to the CTLs. The aforementioned APCs and exosomes can be prepared by methods described above and the method of (4) is detailed bellow in section "VIII. T cell receptor (TCR)".

The CTLs of this invention can be derived from patients who are subject to treatment and/or prevention, and can be administered by themselves or in combination with other drugs including the peptides of this invention or exosomes for the purpose of regulating effects. The obtained CTLs act specifically against target cells presenting the peptides of this invention, for example, the same peptides used for induction. The target cells can be cells that endogenously express C1orf59, such as cancer cells, or cells that are transfected with the C1orf59 gene; and cells that present a peptide of this invention on the cell surface due to stimulation by the peptide can also serve as targets of activated CTL attack.

VIII. T Cell Receptor (TCR)

The present invention also provides a composition containing nucleic acids encoding polypeptides that are capable of forming a subunit of a T cell receptor (TCR), and methods of using the same. The TCR subunits have the ability to form TCRs that confer specificity to T cells against tumor cells expressing C1orf59. By using the known methods in the art, the nucleic acid sequence encoding alpha- and beta-chains of the TCR subunits which are carried by the CTLs induced with peptides of this invention can be identified (WO2007/032255 and Morgan et al., J Immunol, 171, 3288 (2003)). For example, the PCR method is preferred to analyze the nucleic acid sequence encoding the TCR subunits. The PCR primers for the analysis can be, for example, 5'-R primers (5'-gtctac-caggcattcgcttcat-3') as 5' side primers (SEQ ID NO: 44) and 3-TRa-C primers (5'-tcagctggaccacagccgcagcgt-3') specific to TCR alpha chain C region (SEQ ID NO: 45), 3-TRb-C1 primers (5'-tcagaaatcctttctcttgac-3') specific to TCR beta chain C1 region (SEQ ID NO: 46) or 3-TRbeta-C2 primers (5'-ctagcctctggaatcctttctctt-3') specific to TCR beta chain C2 region (SEQ ID NO: 47) as 3' side primers, but not limited. The derivative TCRs can bind target cells displaying the C1orf59 peptide with high avidity, and optionally mediate efficient killing of target cells presenting the C1orf59 peptide in vivo and in vitro.

The nucleic acids encoding the TCR subunits can be incorporated into suitable vectors, e.g., retroviral vectors. These vectors are well known in the art. The nucleic acids or the vectors containing them can be transferred into a T cell, for example, a T cell from a patient, using methods well known in the arts. Advantageously, the present invention provides an off-the-shelf composition allowing rapid modification of a patient's own T cells (or those of another mammal) to rapidly and easily produce modified T cells having excellent cancer cell killing properties.

The TCR encoded by the nucleic acids isolated from a CTL induced by the peptide of the present invention is capable of specifically recognizing a complex of the peptide of the present invention and HLA molecule, giving a T cell specific activity against the target cell when the TCR is carried on the surface of the T cell. Such specific recognition may be confirmed by any known methods, and preferred methods include, for example, tetramer analysis using HLA molecule and the peptide of the present invention (e.g., Altman et al. Science. 274, 94-96 (1996); McMichael et al. J Exp Med. 187, 1367-1371 (1998)), and ELISPOT assay. By performing the ELISPOT assay, it can be confirmed that a T cell expressing the TCR on the cell surface recognizes a cell by the TCR, and the signal is transmitted intracellularly, and then cytokine, such as INF-gamma, is released from the T cell. The cytotoxic activity of the T cell against target cells can be examined using the methods well-know in the arts. A preferred method includes, for example, chromium release assay using HLA positive cells expressing C1orf59 as target cells.

Also, the present invention provides CTLs which are prepared by transduction with the nucleic acids encoding the TCR subunits polypeptides that bind to the C1orf59 peptide of, e.g. SEQ ID NOs: 1, 3, 4, 7, 9, 13, 15, 17 and, 20 in the context of HLA-A02 and also the peptides of SEQ ID NOs: 26, 32, 34, 40 and 41 in the context of HLA-A24. The transduced CTLs are capable of homing to cancer cells in vivo, and can be expanded by well known in vitro culturing methods (e.g., Kawakami et al., J Immunol., 142, 3452-3461 (1989)). The CTLs of the present invention can be used to form an immunogenic composition useful in treating or the prevention of cancer in a patient in need of therapy or protection (WO2006/031221).

IX. Pharmaceutical Agents or Compositions

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis. Treating and/or for the prophylaxis of cancer or, and/or the prevention of postoperative recurrence thereof includes any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

Since C1orf59 expression is specifically elevated in cancers including bladder cancer, breast cancer, cervical cancer, colorectal cancer, esophagus cancer, NSCLC, osteosarcoma, ovarian cancer, pancreatic cancer, prostate cancer and SCLC, as compared with normal tissue, the peptides of the present invention or polynucleotides encoding such peptides can be used for the treatment and/or for the prophylaxis of cancer or tumor, and/or prevention of postoperative recurrence thereof. Thus, the present invention provides a pharmaceutical agent or composition for treating and/or for the prophylaxis of cancer or tumor, and/or prevention of postoperative recurrence thereof, which includes one or more of the peptides of the present invention, or polynucleotides encoding the peptides as an active ingredient. Alternatively, the present peptides can be expressed on the surface of any of the foregoing exosomes or cells, such as APCs for the use as pharmaceutical agents or compositions. In addition, the aforementioned CTLs which target any of the peptides of the invention can also be used as the active ingredient of the present pharmaceutical agents or compositions.

In another embodiment, the present invention also provides the use of an active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention
in manufacturing a pharmaceutical composition or agent for treating cancer or tumor.

Alternatively, the present invention further provides an active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention
for use in treating cancer of tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention
as active ingredients.

In another embodiment, the present invention also provides a method or process for manufacturing a pharmaceutical composition or agent for treating cancer or tumor, wherein the method or process includes the steps of admixing an active ingredient with a pharmaceutically or physiologically acceptable carrier, wherein the active ingredient is selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

Alternatively, the pharmaceutical composition or agent or the present invention may be used for either or both the prophylaxis of cancer or tumor and prevention of post-operative recurrence thereof.

The present pharmaceutical agents or compositions find use as a vaccine. In the context of the present invention, the phrase "vaccine" (also referred to as an "immunogenic composition") refers to a substance that has the function to induce anti-tumor immunity upon inoculation into animals.

The pharmaceutical agents or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides having an amino acid sequence of any one of SEQ ID NOs: 1, 3, 4, 7, 9, 13, 15, 17, 20, 26, 32, 34, 40 and 41 have been found to be HLA-A02 or A24 restricted epitope peptides or candidates that can induce potent and specific immune response. Therefore, the present pharmaceutical agents or compositions which include any of these peptides having the amino acid sequences of SEQ ID NOs: 1, 3, 4, 7, 9, 13, 15, 17 and, 20 are particularly suited for the administration to subjects whose HLA antigen is HLA-A02, and the peptides having the amino acid sequences of SEQ ID NOs: 26, 32, 34, 40 and 41 are particularly suited for the administration to subjects whose HLA antigen is HLA-A24. The same applies to pharmaceutical agents and compositions which include polynucleotides encoding any of these peptides (i.e. the polynucleotides of this invention).

Cancers or tumors to be treated by the pharmaceutical agents or compositions of the present invention are not limited and include all kinds of cancers or tumors wherein C1orf59 is involved, including for example, bladder cancer, breast cancer, cervical cancer, colorectal cancer, esophagus cancer, NSCLC, osteosarcoma, ovarian cancer, pancreatic cancer, prostate cancer and SCLC.

The present pharmaceutical agents or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention can optionally include other therapeutic substances as an active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents or compositions of this invention can include other agents conventional in the art having regard to the type of formulation in question.

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of this invention can be administered directly as a pharmaceutical agent or composition, or if necessary, that has been formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of this invention can be used for anticancer purposes.

The peptides of this invention can be prepared as a combination composed of two or more of the peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs that present any of the peptides of this invention on their cell surface, which may be obtained by stimulating APCs (e.g., DCs) derived from a subject with the peptides of this invention may be administered to the subjects, and as a result, CTLs are induced in the subject and aggressiveness towards the cancer cells can be increased.

The pharmaceutical agents or compositions for the treatment and/or prevention of cancer or tumor, which include a peptide of this invention as the active ingredient, can also include an adjuvant known to effectively induce cellular immunity. Alternatively, the pharmaceutical agents or compositions can be administered with other active ingredients or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Example of suitable adjuvants include aluminum phosphate, aluminum hydroxide, alum, cholera toxin, salmonella toxin, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid.

In some embodiments, the pharmaceutical agents or compositions of the present invention may further include a component which primes CTLs. Lipids have been identified as agents capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, $E.\ coli$ lipoproteins, such as tripalmitoyl-S-glycerylcysteinlyseryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents or Compositions Containing Polynucleotides as the Active Ingredient The pharmaceutical agents or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566;

5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. Methods Using the Peptides, Exosomes, APCs and CTLs

The peptides and polynucleotides of the present invention can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also be used for inducing APCs as discussed explained below.

(1) Method of Inducing Antigen-Presenting Cells (APCs)

The present invention provides methods of inducing APCs with high CTL inducibility using the peptides or polynucleotides of this invention.

The methods of the present invention include the step of contacting APCs with the peptides of this invention in vitro, ex vivo or in vivo. For example, the method contacting APCs with the peptides ex vivo can include the steps of:

a: collecting APCs from a subject; and b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. DCs can be preferably used due to its strongest CTL inducibility among the APCs. Any peptides of the present invention can be used as the peptide of step b by themselves or in combination with other peptides of this invention.

Alternatively, the peptides of the present invention may be administered to a subject to contact the peptides with APCs in vivo. Consequently, APCs with high CTL inducibility can be induced in the body of the subject. Thus, the present invention also contemplates a method of administering the peptides of this invention to a subject to induce APCs in vivo. It is also possible to administer polynucleotides encoding the peptides of this invention to a subject in an expressible form, so that the peptides of this invention are expressed and contacted with APCs in vivo, to consequently induce APCs with high CTL inducibility in the body of the subject. Thus, the present invention also contemplates a method of administering the polynucleotides of this invention to a subject to induce APCs in vivo. The phrase "expressible form" is defined above in section "IX. Pharmaceutical agents (2) Pharmaceutical agents containing polynucleotides as the active ingredient".

Furthermore, the present invention includes introducing the polynucleotide of this invention into an APC to induce APCs with CTL inducibility. For example, the method may include the steps of:

a: collecting APCs from a subject, and b: introducing a polynucleotide encoding a peptide of this invention.

Step b can be performed as described above in section "VI. Antigen-presenting cells".

(2) Method of Inducing CTLs

Furthermore, the present invention provides methods for inducing CTLs using the peptides, polynucleotides, or exosomes or APCs of this invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs include at least one step selected from the group consisting of:

a) contacting a CD8-positive T cell with an antigen-presenting cell and/or an exosome that presents on its surface a complex of an HLA antigen and a peptide of the preset invention; and b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the present invention also contemplates a method which includes the step of administering the peptides, the polynucleotides, the APCs or exosomes of this invention to a subject to induce CTLs.

Alternatively, CTLs can be also induced by their ex vivo use. In such case, after the induction of CTLs, the activated CTLs would be returned to the subject. For example, a method of the present invention to induce CTLs can include steps of:

a) collecting APCs from a subject;
b) contacting the APCs of step a) with the peptide; and
c) co-culturing the APCs of step b with CD8-positive cells.

The APCs to be co-cultured with the CD8-positive cells in above step c can also be prepared by transferring a gene that includes a polynucleotide of this invention into APCs as described above in section "VI. Antigen-presenting cells"; but are not limited thereto and any APCs which effectively presents on its surface a complex of an HLA antigen and the peptide of this invention can be used for the instant method.

Instead of such APCs, the exosomes that presents on its surface a complex of an HLA antigen and the peptide of this invention can be also used. Namely, the present invention also contemplates a method wherein exosomes presenting on its surface a complex of an HLA antigen and the peptide of this invention are co-cultured with CD8-positive cells. Such exosomes may be prepared by the methods described above in section "V. Exosomes".

Furthermore, CTL can be induced by introducing a gene that includes a polynucleotide encoding the TCR subunit binding to the peptide of this invention into CD8-positive cells. Such transduction can be performed as described above in section "VIII. T cell receptor (TCR)".

In addition, the present invention provides a method or process for manufacturing a pharmaceutical agent or composition inducing CTLs, wherein the method includes the step of admixing or formulating the peptide of the present invention with a pharmaceutically acceptable carrier.

(3) Method of Inducing Immune Response

Moreover, the present invention provides methods for inducing immune response against diseases related to C1orf59. Suitable disease include cancer, examples of which include bladder cancer, breast cancer, cervical cancer, colorectal cancer, esophagus cancer, NSCLC, osteosarcoma, ovarian cancer, pancreatic cancer, prostate cancer and SCLC.

The methods include the step of administering agents or compositions containing any of the peptides of the present invention or polynucleotides encoding them. The present inventive method also contemplates the administration of exosomes or APCs presenting any of the peptides of the present invention. For details, see the item of "IX. Pharmaceutical agents or compositions", particularly the part describing the use of the pharmaceutical agents and compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical agent or composition inducing immune response, wherein the method includes the step of admixing or formulating the peptide of the present invention with a pharmaceutically acceptable carrier.

Althernatively, the method of the present invention may include the step of administrating a vaccine or a pharmaceutical composition, which contains:

(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention In the present invention, cancer overexpressing C1orf59 can be treated with these active ingredients. The cancer includes, but is not limited to, bladder cancer, breast cancer, cervical cancer, colorectal cancer, esophagus cancer, non-small cell lung cancer (NSCLC), osteosarcoma, ovarian cancer, pancreatic cancer, prostate cancer, and small cell lung cancer (SCLC). Accordingly, prior to the administration of the vaccines or pharmaceutical compositions comprising the active ingredients, it is preferable to confirm whether the expression level of C1orf59 in the cancer cells or tissues to be treated is enhanced compared with normal cells of the same organ. Thus, in one embodiment, the present invention provides a method for treating cancer (over) expressing C1orf59, which method may include the steps of:

i) determining the expression level of C1orf59 in cancer cells or tissue(s) obtained from a subject with the cancer to be treated;
ii) comparing the expression level of C1orf59 with normal control; and
iii) administrating at least one component selected from the group consisting of (a) to (d) described above to a subject with cancer overexpressing C1orf59 compared with normal control.

Alternatively, the present invention also provides a vaccine or pharmaceutical composition comprising at least one component selected from the group consisting of (a) to (d) described above, for use in administrating to a subject having cancer overexpressing C1orf59. In other words, the present invention further provides a method for identifying a subject to be treated with the C1orf59 polypeptide of the present invention, which method may include the step of determining an expression level of C1orf59 in subject-derived cancer cells or tissue, wherein an increase of the level compared to a normal control level of the gene indicates that the subject has cancer which may be treated with the C1orf59 polypeptide of the present invention.

According to the present invention, the expression level of C1orf59 in the cancer cells or tissues obtained from a subject is determined. The expression level can be determined at the transcription (nucleic acid) product level, using methods known in the art. For example, the mRNA of C1orf59 may be quantified using probes by hybridization methods (e.g., Northern hybridization). The detection may be carried out on a chip or an array. The use of an array is preferable for detecting the expression level of C1orf59. Those skilled in the art can prepare such probes utilizing the sequence information of C1orf59. For example, the cDNA of C1orf59 may be used as the probes. If necessary, the probe may be labeled with a suitable label, such as dyes, fluorescent substances and isotopes, and the expression level of the gene may be detected as the intensity of the hybridized labels.

Furthermore, the transcription product of C1orf59 may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of C1orf59. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the determination of the C1orf59 expression level. For example, the quantity of C1orf59 protein may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment or modified antibody retains the binding ability to C1orf59 protein. Methods to prepare these kinds of antibodies for the detection of proteins are well known in the art, and any method may be employed in the present invention to prepare such antibodies and equivalents thereof.

As another method to detect the expression level of C1orf59 gene based on its translation product, the intensity of staining may be observed via immunohistochemical analysis using an antibody against C1orf59 protein. Namely, in this measurement, strong staining indicates increased presence/level of the protein and, at the same time, high expression level of C1orf59 gene.

The expression level of C1orf59 gene in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the cancer cells by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of C1orf59 gene in samples from subjects whose disease states are known. Furthermore, the control level can be derived from a database of expression patterns from previously tested cells.

Moreover, according to an aspect of the present invention, the expression level of C1orf59 gene in a subject-derived sample may be compared to multiple control levels, which are determined from multiple reference samples. It is preferred to use a control level determined from a reference sample derived from a tissue type similar to that of the subject-derived sample. Moreover, it is preferred, to use the standard value of the expression levels of C1orf59 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level".

When the expression level of C1orf59 gene is increased as compared to the normal control level, or is similar/equivalent to the cancerous control level, the subject is preferably treated with a vaccine or pharmaceutical composition of the present invention.

More specifically, the present invention provides a method of (i) diagnosing whether a subject has the cancer to be treated, and/or (ii) selecting a subject for cancer treatment, which method includes the steps of:

a) determining the expression level of C1orf59 in cancer cells or tissue(s) obtained from a subject who is suspected to have the cancer to be treated;

b) comparing the expression level of C1orf59 with a normal control level;

c) diagnosing the subject as having the cancer to be treated, if the expression level of C1orf59 is increased as compared to the normal control level; and d) selecting the subject for cancer treatment, if the subject is diagnosed as having the cancer to be treated, in step c).

Alternatively, such a method includes the steps of:

a) determining the expression level of C1orf59 in cancer cells or tissue(s) obtained from a subject who is suspected to have the cancer to be treated;

b) comparing the expression level of C1orf59 with a cancerous control level;

c) diagnosing the subject as having the cancer to be treated, if the expression level of C1orf59 is similar or equivalent to the cancerous control level; and d) selecting the subject for cancer treatment, if the subject is diagnosed as having the cancer to be treated, in step c).

The present invention also provides a kit for determining a subject suffering from cancer that can be treated with the C1orf59 polypeptide of the present invention, which may also be useful in assessing and/or monitoring the efficacy of a cancer immunotherapy. Preferably, the cancer includes, but is not limited to, bladder cancer, breast cancer, cervical cancer, colorectal cancer, esophagus cancer, non-small cell lung cancer (NSCLC), osteosarcoma, ovarian cancer, pancreatic cancer, prostate cancer, and small cell lung cancer (SCLC). More particularly, the kit preferably includes at least one reagent for detecting the expression of the C1orf59 gene in a subject-derived cancer cell, which reagent may be selected from the group of:

(a) a reagent for detecting mRNA of the C1orf59 gene;
(b) a reagent for detecting the C1orf59 protein; and
(c) a reagent for detecting the biological activity of the C1orf59 protein.

Suitable reagents for detecting mRNA of the C1orf59 gene include nucleic acids that specifically bind to or identify the C1orf59 mRNA, such as oligonucleotides which have a complementary sequence to a portion of the C1orf59 mRNA. These kinds of oligonucleotides are exemplified by primers and probes that are specific to the C1orf59 mRNA. These kinds of oligonucleotides may be prepared based on methods well known in the art. If needed, the reagent for detecting the C1orf59 mRNA may be immobilized on a solid matrix. Moreover, more than one reagent for detecting the C1orf59 mRNA may be included in the kit.

On the other hand, suitable reagents for detecting the C1orf59 protein include antibodies to the C1orf59 protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment or modified antibody retains the binding ability to the C1orf59 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the C1orf59 protein may be included in the kit.

The kit may contain more than one of the aforementioned reagents. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In an embodiment of the present invention, when the reagent is a probe against the C1orf59 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of C1orf59 mRNA present in the sample. The detection sites may be configured in any suitably detectable shape and are typically in the shape of a bar or dot spanning the width of a test strip.

The kit of the present invention may further include a positive control sample or C1orf59 standard sample. The positive control sample of the present invention may be prepared by collecting C1orf59 positive samples and then assaying their C1orf59 levels. Alternatively, a purified C1orf59 protein or polynucleotide may be added to cells that do not express C1orf59 to form the positive sample or the C1orf59 standard sample. In the present invention, purified C1orf59 may be a recombinant protein. The C1orf59 level of the positive control sample is, for example, more than the cut off value.

The following examples are presented to illustrate the present invention and to assist one of ordinary skill in making and using the same. The examples are not intended in any way to otherwise limit the scope of the invention.

EXAMPLES

Example 1

Materials and Methods

Cell Lines

T2 (HLA-A2), human B-lymphoblastoid cell line, and COS7, African green monkey kidney cell line, were purchased from ATCC.

Candidate Selection of Peptides Derived from C1orf59

9-mer and 10-mer peptides derived from C1orf59 that bind to HLA-A*0201 molecule were predicted using binding prediction software "BIMAS" (world wide web—bimas.cit.nih.gov/molbio/hla_bind) (Parker et al., J Immunol 1994, 152 (1): 163-75), Kuzushima et al., Blood 2001, 98(6): 1872-81)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (GM-CSF) (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro grams/ml of each of the synthesized peptides in the presence of 3 micro grams/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way as described above. CTL was tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of 5×10⁴ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with 1×10⁴ cells/well of 2 kinds of human B-lymphoblastoid cell lines, 30 ng/ml of anti-CD3 antibody, and 125 U/ml of IL-2 in a total of 150 microlitter/well of AIM-V Medium containing 5% AS. 50 microlitter/well of IL-2 was added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 (1×10⁴/well) was prepared as stimulator cells. Cultured cells in 48 wells were used as responder cells. IFN-gamma ELISPOT assay and IFN-gamma ELISA assay were performed under manufacture procedures.

Preparation of the Cells Exogenously Expressing Either or Both of the Target Gene and HLA-A02

The cDNA encoding an open reading frame of target genes or HLA-A02 was amplified by PCR. The PCR-amplified product was cloned into pCAGGS vector. The plasmids were transfected into COS7, which is the target genes and HLA-A02-null cell line, using lipofectamine 2000 (Invitrogen) according to the manufacturer's recommended procedures. After 2 days from transfection, the transfected cells were harvested with versene (Invitrogen) and used as the target cells (5×10⁴ cells/well) for CTL activity assay.

Results

Enhanced C1orf59 Expression in Cancers

The global gene expression profile data obtained from various cancers using cDNA-microarray revealed that C1orf59 (GenBank Accession No. NM_144584; SEQ ID No: 42) expression was elevated. C1orf59 expression was validly elevated in 31 out of 33 bladder cancers, 34 out of 70 breast cancers, 11 out of 12 cervical cancers, 8 out of 8 colorectal cancers, 25 out of 57 esophageal cancers, 2 out of 10 NSCLCs, 8 out of 16 osteosarcomas, 1 out of 1 ovarian cancers, 3 out of 6 pancreatic cancers, 20 out of 41 prostate cancers, 7 out of 13 SCLCs and 25 out of 34 soft tissue tumors as compared with corresponding normal tissue (Table 1).

TABLE 1

Ratio of cases observed up-regulation of C1orf59 in cancerous tissue as compared with normal corresponding tissue

| Cancers | Ratio |
| --- | --- |
| Bladder Cancer | 31/33 |
| Breast Cancer | 34/70 |
| Cervical Cancer | 11/12 |
| Colorectal Cancer | 8/8 |
| Esophagus Cancer | 25/57 |
| NSCLC | 2/10 |
| Osteosarcoma | 8/16 |
| Ovarian Cancer | 1/1 |
| Pancreatic Cancer | 3/6 |
| Prostate Cancer | 20/41 |
| SCLC | 7/13 |

Prediction of HLA-A02 Binding Peptides Derived from C1orf59

Table 2 shows the HLA-A02 binding peptides of C1orf59 in the order of high binding affinity. A total of 24 peptides with potential HLA-A02 binding ability were selected and examined to determine the epitope peptides (Table 2).

TABLE 2

HLA-A02 binding 9mer and 10mer peptides derived from C1orf59

| Peptide name | Rank | Start Position | Amino acid sequence | BIMAS score | SEQ ID NO |
| --- | --- | --- | --- | --- | --- |
| C1orf59-9mer | 1 | 261 | LQQERFFKL | 166.362 | 1 |
|  | 2 | 333 | FCVGDKFFV | 66.623 | 2 |
|  | 3 | 152 | YLSPSMIVI | 45.255 | 3 |
|  | 4 | 121 | RLLGFDLIT | 42.958 | 4 |
|  | 5 | 271 | LVNEVSQQV | 42.418 | 5 |
|  | 6 | 63 | RLLKVNPCI | 38.601 | 6 |
|  | 7 | 122 | LLGFDLITC | 19.425 | 7 |
| C1orf59-10mer | 1 | 261 | LQQErFFKLV | 354.871 | 8 |
|  | 2 | 240 | CLSEqHDQHV | 285.163 | 9 |
|  | 3 | 260 | SLQQeRFFKL | 235.414 | 10 |
|  | 4 | 270 | VLVNeVSQQV | 118.238 | 11 |
|  | 5 | 346 | LLAYpKLNRL | 83.527 | 12 |
|  | 6 | 90 | SLAPfLGDFL | 57.572 | 13 |
|  | 7 | 334 | CVGDkFFVPL | 55.332 | 14 |
|  | 8 | 188 | MEFQtWALYV | 46.786 | 15 |
|  | 9 | 121 | RLLGfDLITC | 42.278 | 16 |
|  | 10 | 122 | LLGFdLITCI | 40.792 | 17 |
|  | 11 | 30 | PLYRqRYQFV | 40.396 | 18 |
|  | 12 | 183 | FEWTrMEFQT | 32.087 | 19 |
|  | 13 | 196 | YVANrYDYSV | 27.995 | 20 |

TABLE 2-continued

HLA-A02 binding 9mer and 10mer peptides derived from C1orf59

| Peptide name | Start Rank Position | Amino acid sequence | BIMAS score | SEQ ID NO |
|---|---|---|---|---|
| | 14 | 10 | SVVDgNFEEV | 23.23 | 21 |
| | 15 | 66 | KVNPcIELLV | 21.3 | 22 |
| | 16 | 326 | IENSpTPFCV | 13.335 | 23 |
| | 17 | 252 | AVFTtSYPSL | 10.374 | 24 |

Start position indicates the number of amino acid residue from the N-terminus of C1orf59.
Binding score is derived from "BIMAS".

CTL Induction With the Predicted Peptides from C1orf59 Restricted with HLA-A*0201

Figure 1:
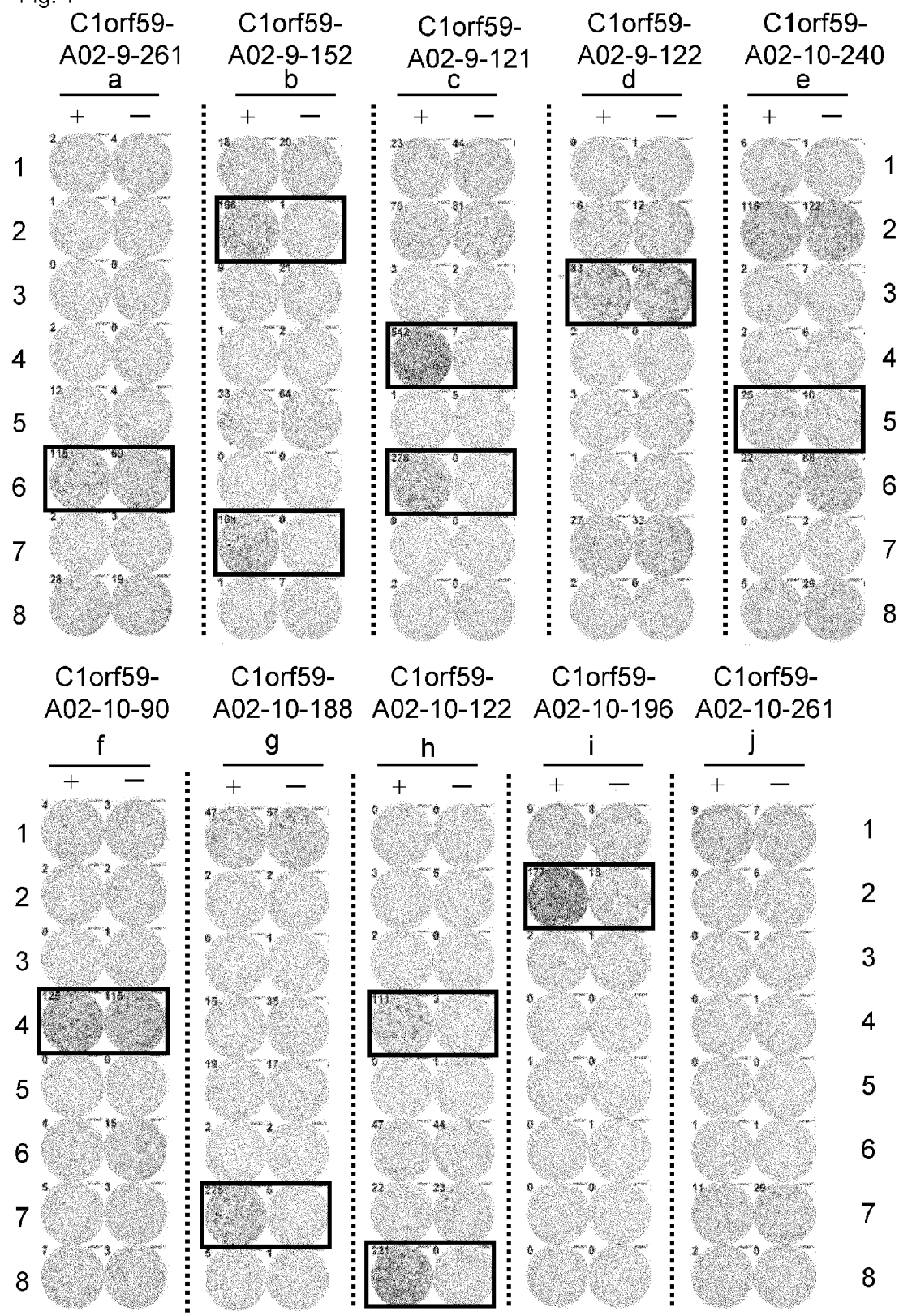
FIG. 1 includes a series of photographs (a)-(j) depicting the results of IFN-gamma ELISPOT assay on CTLs that were induced with peptides derived from C1orf59. The CTLs in well number #6 stimulated with C1orf59-A02-9-261 (SEQ ID NO: 1) (a), #2 and #7 with C1orf59-A02-9-152 (SEQ ID NO: 3) (b), #4 and #6 with C1orf59-A02-9-121 (SEQ ID NO 4) (c), #3 with C1orf59-A02-9-122 (SEQ ID NO 7) (d), #5 with C1orf59-A02-10-240 (SEQ ID NO: 9) (e), #4 with C1orf59-A02-10-90 (SEQ ID NO: 13) (f), #7 with C1orf59-A02-10-188 (SEQ ID NO: 15) (g), #4 and #8 with C1orf59-A02-10-122 (SEQ ID NO: 17) (h), and #2 with C1orf59-A02-10-196 (SEQ ID NO: 20) (i) showed potent IFN-gamma production as compared with the control, respectively. The cells in the wells denoted with a rectangular box were expanded to establish CTL lines. In contrast, as a typical case of negative data, no specific IFN-gamma production were detected for CTL stimulated with C1orf59-A02-10-261 (SEQ ID NO: 8) (j). In the figures., "+" indicates the IFN-gamma production against target cells pulsed with the appropriate peptide, and "−" indicates that the IFN-gamma production against target cells had not been pulsed with any peptides.
Figure 2:
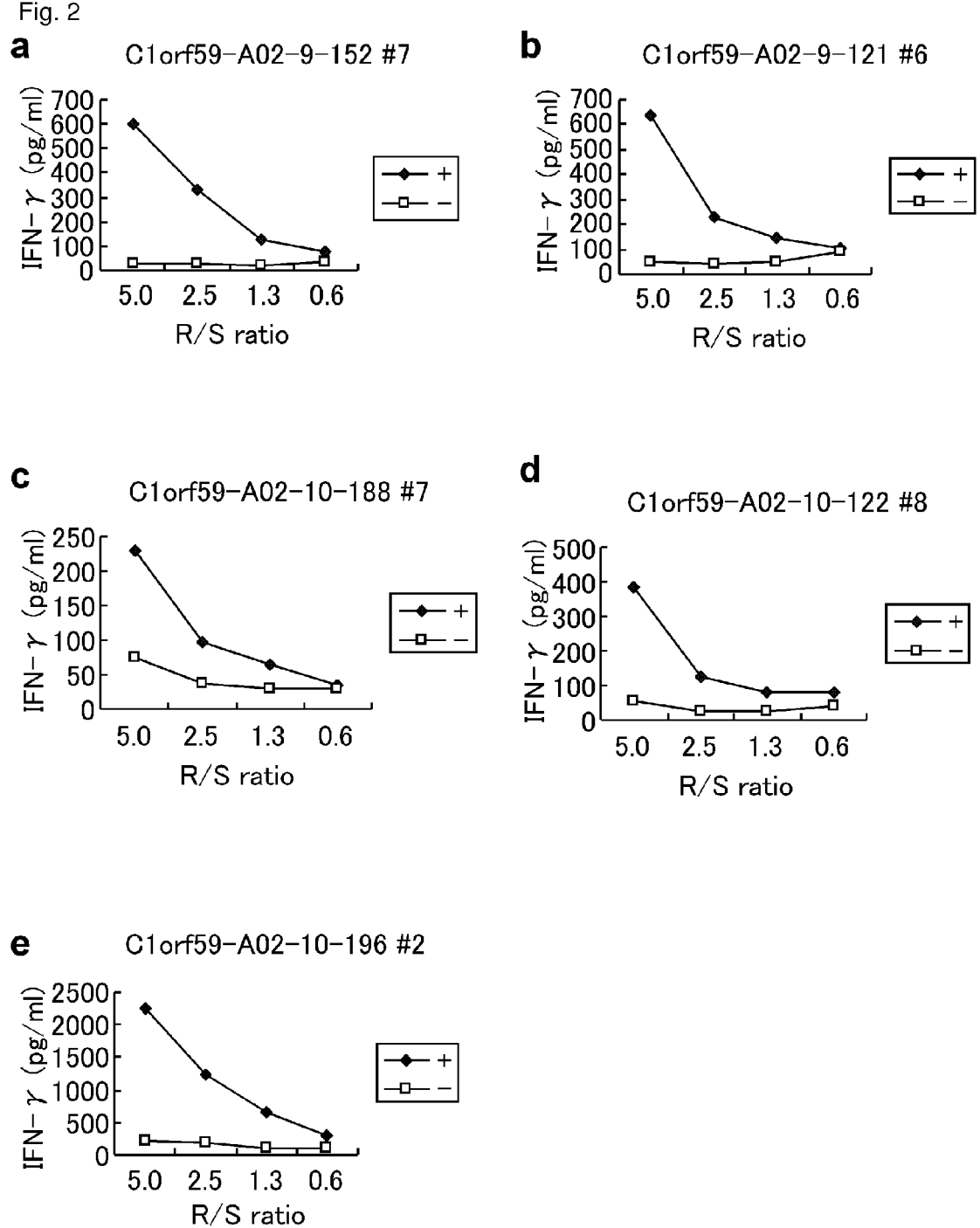
FIG. 2 includes a series of line graphs (a)-(e) depicting the IFN-gamma production of CTL lines stimulated with C1orf59-A02-9-152 (SEQ ID NO: 3) (a), C1orf59-A02-9-121 (SEQ ID NO: 4) (b), C1orf59-A02-10-188 (SEQ ID NO: 15) (c), C1orf59-A02-10-122 (SEQ ID NO: 17) (d), and C1orf59-A02-10-196 (SEQ ID NO: 20) (e) with IFN-gamma ELISA assay. CTL lines established by stimulation with each peptide showed potent IFN-gamma production as compared with the control. In the figures., "+" indicates the IFN-gamma production against target cells pulsed with the appropriate peptide and "−" indicates that the IFN-gamma production against target cells had not been pulsed with any peptides.

CTLs for those peptides derived from C1orf59 were generated according to the protocols as described in "Materials and Methods". Peptide specific CTL activity was determined by IFN-gamma ELISPOT assay (FIG. 1(a)-(i)). It showed that the well number #6 stimulated with C1orf59-A02-9-261 (SEQ ID NO: 1) (a), #2 and #7 with C1orf59-A02-9-152 (SEQ ID NO: 3) (b), #4 and #6 with C1orf59-A02-9-121 (SEQ ID NO: 4) (c), #3 with C1orf59-A02-9-122 (SEQ ID NO: 7) (d), #5 with C1orf59-A02-10-240 (SEQ ID NO: 9) (e), #4 with C1orf59-A02-10-90 (SEQ ID NO: 13) (f), #7 with C1orf59-A02-10-188 (SEQ ID NO: 15) (g), #4 and #8 with C1orf59-A02-10-122 (SEQ ID NO: 17) (h), and #2 with C1orf59-A02-10-196 (SEQ ID NO: 20) (i) demonstrated potent IFN-gamma production as compared to the control wells. On the other hand, no specific CTL activity was determined by stimulation with other peptides shown in Table 1, despite those peptide had possible binding activity with HLA-A*0201. As a typical case of negative data, specific IFN-gamma production was not detected for the CTL stimulated with C1orf59-A02-10-261 (SEQ ID NO: 8) (FIG. 1(j)). As a result, 9 peptides derived from C1orf59 were screened as peptides that could induce potent CTLs.

Establishment of CTL Lines and Clones Against C1orf59 Specific Peptides

Figure 3:
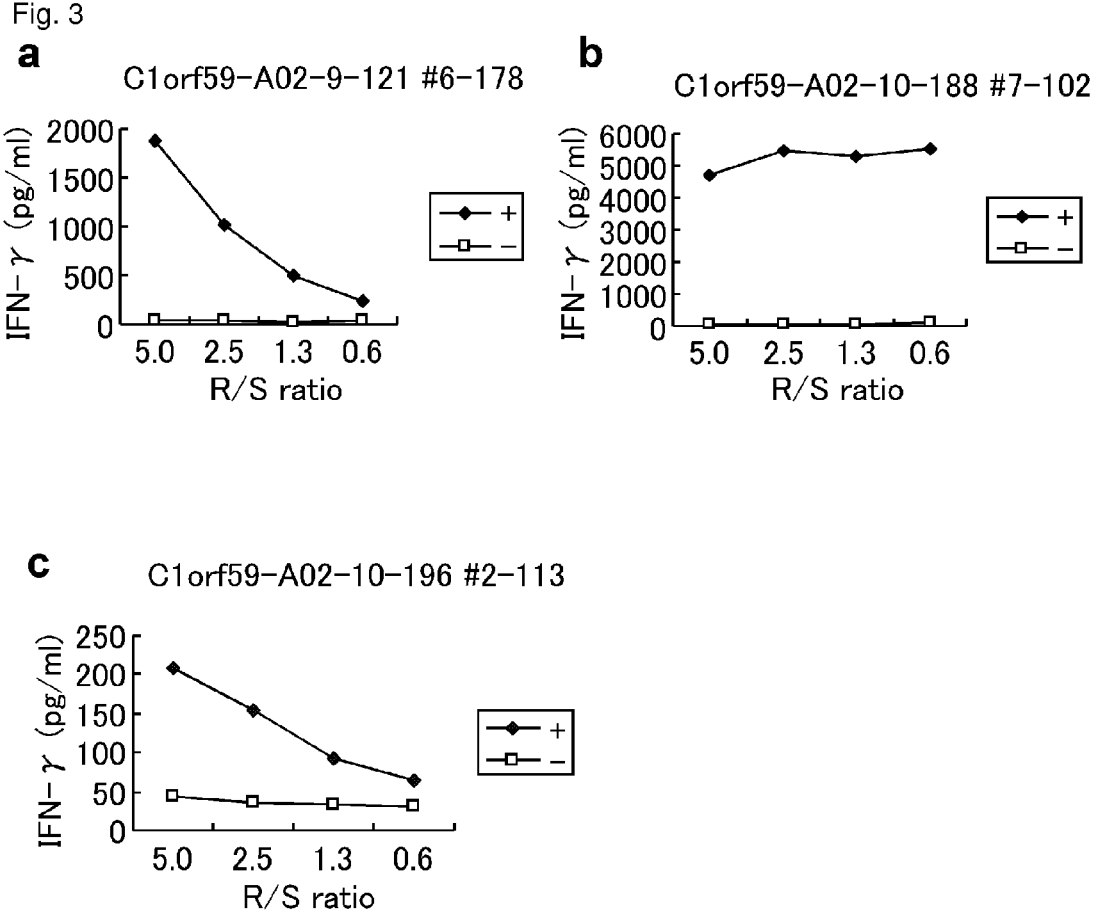
FIG. 3 depicts the IFN-gamma production of the CTL clones established by limiting dilution from the CTL lines stimulated with C1orf59-A02-9-121 (SEQ ID NO: 4) (a), C1orf59-A02-10-188 (SEQ ID NO: 15) (b) and C1orf59-A02-10-196 (SEQ ID NO: 20) (c). The results depicted herein demonstrate that the CTL clones established by stimulation with each of the peptides showed potent IFN-gamma production as compared with the control. In the figure, "+" indicates the IFN-gamma production against target cells pulsed with the appropriate peptide and "−" indicates that the IFN-gamma production against target cells had not been pulsed with any peptides.

The cells that showed peptide specific CTL activity detected by IFN-gamma ELISPOT assay in the well number #7 with C1orf59-A02-9-152 (SEQ ID NO: 3), #6 with C1orf59-A02-9-121 (SEQ ID NO: 4), #7 with C1orf59-A02-10-188 (SEQ ID NO: 15), #8 with C1orf59-A02-10-122 (SEQ ID NO: 17) and #2 with C1orf59-A02-10-196 (SEQ ID NO: 20) were expanded and established as CTL lines. Each CTL activity of those CTL lines was determined by IFN-gamma ELISA assay (FIG. 2(a)-(e)). It showed that all CTL lines demonstrated potent IFN-gamma production against the target cells pulsed with corresponding peptide as compared to target cells without peptide pulse. Furthermore, CTL clones were established by limiting dilution from CTL lines as described in "Materials and Methods", and IFN-gamma production from CTL clones against target cells pulsed peptide were determined by IFN-gamma ELISA assay (FIG. 3(a)-(c)). Potent IFN-gamma productions were determined from CTL clones stimulated with C1orf59-A02-9-121 (SEQ ID NO: 4), C1orf59-A02-10-188 (SEQ ID NO: 15) and C1orf59-A02-10-196 (SEQ ID NO: 20).

Specific CTL Activity Against Target Cells Exogenously Expressing C1orf59 and HLA-A*0201

The established CTL lines raised against these peptides were examined for their ability to recognize target cells that endogenously express C1orf59 and HLA-A*0201 molecule. Specific CTL activity against COS7 cells which were transfected with both the full length of C1orf59 and HLA-A*0201 molecule gene (a specific model for the target cells that exogenously express C1orf59 and HLA-A*0201 gene) was tested using the CTL lines raised by corresponding peptide as the effecter cells. COS7 cells transfected with either full length of C1orf59 genes or HLA-A*0201 were prepared as control. In FIG. 4, the CTLs stimulated with C1orf59-A02-9-152 (SEQ ID NO: 3) (a), C1orf59-A02-9-121 (SEQ ID NO: 4) (b) and C1orf59-A02-10-188 (SEQ ID NO: 15) (c) showed potent CTL activity against COS7 cells expressing both C1orf59 and HLA-A*0201. On the other hand, no significant specific CTL activity was detected against the controls. Thus, these data clearly demonstrate that C1orf59-A02-9-152 (SEQ ID NO: 3), C1orf59-A02-9-121 (SEQ ID NO: 4) and C1orf59-A02-10-188 (SEQ ID NO: 15) are naturally expressed on the target cells with HLA-A*0201 molecule and are recognized by the CTLs. These results indicate that these peptides derived from C1orf59 may be available to apply the cancer vaccines for patients with C1orf59 expressing tumors.

Homology Analysis of Antigen Peptides

The CTLs stimulated with

C1orf59-A02-9-261 (SEQ ID NO: 1),

C1orf59-A02-9-152 (SEQ ID NO: 3),

C1orf59-A02-9-121 (SEQ ID NO: 4),

C1orf59-A02-9-122 (SEQ ID NO: 7),

C1orf59-A02-10-240 (SEQ ID NO: 9),

C1orf59-A02-10-90 (SEQ ID NO: 13),

C1orf59-A02-10-188 (SEQ ID NO: 15),

C1orf59-A02-10-122 (SEQ ID NO: 17) and

C1orf59-A02-10-196 (SEQ ID NO: 20) showed significant and specific CTL activity. This result may be due to the fact that the sequences of C1orf59-A02-9-261 (SEQ ID NO: 1), C1orf59-A02-9-152 (SEQ ID NO: 3), C1orf59-A02-9-121 (SEQ ID NO: 4), C1orf59-A02-9-122 (SEQ ID NO: 7), C1orf59-A02-10-240 (SEQ ID NO: 9), C1orf59-A02-10-90 (SEQ ID NO: 13), C1orf59-A02-10-188 (SEQ ID NO: 15), C1orf59-A02-10-122 (SEQ ID NO: 17) and C1orf59-A02-10-196 (SEQ ID NO: 20) are homologous to peptides derived from other molecules that are known to sensitize the human immune system. To exclude this possibility, homology analyses were performed for these peptide sequences using as queries the BLAST algorithm (world wide web—ncbi.nlm.nih.gov/blast/blast.cgi) which revealed no sequence with significant homology. The results of homology analyses indicate that the sequences of C1orf59-A02-9-261 (SEQ ID NO: 1), C1orf59-A02-9-152 (SEQ ID NO: 3), C1orf59-A02-9-121 (SEQ ID NO: 4), C1orf59-A02-9-122 (SEQ ID NO: 7), C1orf59-A02-10-240 (SEQ ID NO: 9), C1orf59-A02-10-90 (SEQ ID NO: 13), C1orf59-A02-10-188 (SEQ ID NO: 15), C1orf59-A02-10-122 (SEQ ID NO: 17) and C1orf59-A02-10-196 (SEQ ID NO: 20) are unique and thus, there is little possibility, to our best knowledge, that these molecules raise unintended immunologic responses to some unrelated molecules.

In conclusion, novel HLA-A02 epitope peptide derived from C1orf59 were identified and demonstrated to be applicable for cancer immunotherapy.

Example 2

Materials and Methods

Cell Lines

A24 lymphoblastoid cell line (A24LCL) was established by transformation with Epstein-bar virus into HLA-A24 positive human B lymphocyte. COS7, African green monkey kidney cell line, was purchased from ATCC.

Candidate Selection of Peptides Derived from C1orf59

9-mer and 10-mer peptides derived from C1orf59 that bind to HLA-A*2402 molecule were predicted using binding prediction software "BIMAS" ((world wide web—bimas.citnih.gov/molbio/hla_bind) (Parker et al. (J Immunol 1994, 152 (1): 163-75), Kuzushima et al.(Blood 2001, 98(6): 1872-81)). These peptides were synthesized by Sigma (Sapporo, Japan) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro gram/ml of each of the synthesized peptides in the presence of 3 micro gram/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed A24 LCL or T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506)

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 microlitter/well of AIM-V Medium containing 5% AS. 50 microlitter/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed A24 LCL ($1 \times 10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A24

The cDNA encoding an open reading frame of target genes or HLA-A24 was amplified by PCR. The PCR-amplified product was cloned into pCAGGS vector. The plasmids were transfected into COS7, which is the target genes and HLA-A24-null cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Results

Prediction of HLA-A24 Binding Peptides Derived from C1orf59

Table 3 shows the HLA-A24 binding peptides of C1orf59 in the order of high binding affinity. A total of 17 peptides with potential HLA-A24 binding ability were selected and examined to determine the epitope peptides (Table 3).

TABLE 3

HLA-A24 binding 9mer and 10mer peptides derived from C1orf59

| Peptide name | Rank | Start Position | Amino Acid sequence | Binding Score | SEQ ID NO. |
|---|---|---|---|---|---|
| C1orf59-A24-9mer | 1 | 385 | NYFDEQFEF | 132 | 25 |
|  | 2 | 221 | GYCTQIGIF | 100 | 26 |

TABLE 3-continued

HLA-A24 binding 9mer and 10mer peptides derived from C1orf59

| Peptide name | Rank | Start Position | Amino Acid sequence | Binding Score | SEQ ID NO. |
|---|---|---|---|---|---|
| | 3 | 338 | KFFVPLQRL | 48 | 27 |
| | 4 | 339 | FFVPLQRLL | 43.2 | 28 |
| | 5 | 182 | KFEWTRMEF | 33 | 29 |
| | 6 | 35 | RYQFVKNLV | 25.2 | 30 |
| | 7 | 253 | VFTTSYPSL | 20 | 31 |
| | 8 | 66 | KVNPCIELL | 14.4 | 32 |
| | 9 | 145 | FPEVVFGYL | 10.08 | 33 |
| | 10 | 200 | RYDYSVEFT | 10 | 34 |
| C1orf59-A24-10mer | 1 | 257 | SYPSLQQERF | 150 | 35 |
| | 2 | 144 | RFPEVVFGYL | 120.96 | 36 |
| | 3 | 151 | GYLFPSMIVI | 75 | 37 |
| | 4 | 338 | KFFVPLQRLL | 48 | 38 |
| | 5 | 97 | DFLKPRDLNL | 30 | 39 |
| | 6 | 124 | GFDLITCIEL | 22 | 40 |
| | 7 | 363 | RSVIADSIPL | 12 | 41 |

Start position indicates the number of amino acid residue from the N-terminus of C1orf59.
Binding score is derived from "BIMAS".

CTL Induction with the Predicted Peptides from C1orf59 Restricted with HLA-A*2402 and Establishment for CTL Lines Stimulated with C1orf59 Derived Peptides CTLs for those peptides derived from C1orf59 were generated according to the protocols as described in "Materials and Methods". Peptide specific CTL activity was determined by IFN-gamma ELISPOT assay (FIG. 5a-e). It showed that the well number #5 stimulated with C1orf59-A24-9-221 (SEQ ID NO: 26) (a), #3 with C1orf59-A24-9-66 (SEQ ID NO: 32) (b), #4 with C1orf59-A24-9-200 (SEQ ID NO: 34) (c), #5 with C1orf59-A24-10-124 (SEQ ID NO: 40) (d) and #7 with C1orf59-A24-10-363 (SEQ ID NO: 41) (e) demonstrated potent IFN-gamma production as compared to the control wells. Furthermore, all of these cells in the positive wells were expanded and established CTL lines. CTL activity of those CTL lines was determined by IFN-gamma ELISA assay (FIG. 6a-e). It showed that all CTL lines demonstrated potent IFN-gamma production against the target cells pulsed with corresponding peptide as compared to target cells without peptide pulse. On the other hand, no CTL lines could be established by stimulation with other peptides shown in Table 3, despite those peptide had possible binding activity with HLA-A*2402 (data not shown). As a result, it indicated that 5 peptides derived from C1orf59 were screened as the peptides that could induce potent CTL lines.

Establishment of CTL Clones Against C1orf59 Specific Peptides

CTL clones were established by limiting dilution from CTL lines as described in "Materials and Methods", and IFN-gamma production from CTL clones against target cells pulsed peptide were determined by IFN-gamma ELISA assay. Potent IFN-gamma productions were determined from CTL clones stimulated with C1orf59-A24-9-221 (SEQ ID NO: 26), C1orf59-A24-9-66 (SEQ ID NO: 32), C1orf59-A24-9-200 (SEQ ID NO: 34), C1orf59-A24-10-124 (SEQ ID NO: 40) and C1orf59-A24-10-363 (SEQ ID NO: 41) in FIG. 7.

Specific CTL Activity Against Target Cells Exogenously Expressing C1orf59 and HLA-A*2402

The established CTL lines raised against these peptides were examined for their ability to recognize target cells that express C1orf59 and HLA-A*2402 molecule. Specific CTL activity against COS7 cells which transfected with both the full length of C1orf59 and HLA-A*2402 molecule gene (a specific model for the target cells that express C1orf59 and HLA-A*2402 gene) was tested using the CTL lines raised by corresponding peptide as the effecter cells. COS7 cells transfected with either full length of C1orf59 genes or HLA-A*2402 were prepared as control. In FIG. 8, the CTLs stimulated with SEQ ID NO: 26 showed potent CTL activity against COS7 cells expressing both C1orf59 and HLA-A*2402. On the other hand, no significant specific CTL activity was detected against the controls. Thus, these data clearly demonstrated that C1orf59-A24-9-221 (SEQ ID NO: 26) was naturally cleavaged and expressed on the target cells with HLA-A*2402 molecule, and the complex was recognized by the CTLs. These results indicate that this peptide derived from C1orf59 may be available to apply the cancer vaccines for patients with C1orf59 expressing tumors.

Homology Analysis of Antigen Peptides

The CTLs stimulated with C1orf59-A24-9-221 (SEQ ID NO: 26), C1orf59-A24-9-66 (SEQ ID NO: 32), C1orf59-A24-9-200 (SEQ ID NO: 34), C1orf59-A24-10-124 (SEQ ID NO: 40) and C1orf59-A24-10-363 (SEQ ID NO: 41) showed significant and specific CTL activity. This result may be due to the fact that the sequences of C1orf59-A24-9-221 (SEQ ID NO: 26), C1orf59-A24-9-66 (SEQ ID NO: 32), C1orf59-A24-9-200 (SEQ ID NO: 34), C1orf59-A24-10-124 (SEQ ID NO: 40) and C1orf59-A24-10-363 (SEQ ID NO: 41) are homologous to peptides derived from other molecules that are known to sensitize the human immune system. To exclude this possibility, homology analyses were performed for these peptide sequences using as queries the BLAST algorithm (world wide web—ncbi.nlm.nih.gov/blast/blast.cgi) which revealed no sequence with significant homology. The results of homology analyses indicate that the sequences of C1orf59-A24-9-221 (SEQ ID NO: 26), C1orf59-A24-9-66 (SEQ ID NO: 32), C1orf59-A24-9-200 (SEQ ID NO: 34), C1orf59-A24-10-124 (SEQ ID NO: 40) and C1orf59-A24-10-363 (SEQ ID NO: 41) are unique and thus, there is little possibility, to our best knowledge, that these molecules raise unintended immunologic response to some unrelated molecule.

In conclusion, the novel HLA-A24 epitope peptides derived from C1orf59 were identified. Furthermore, it was demonstrated that epitope peptides of C1orf59 may be applicable for cancer immunotherapy.

INDUSTRIAL APPLICABILITY

The present invention describes new TAAs, particularly those derived from C1orf59 which induce potent and specific anti-tumor immune responses and have applicability to a wide array of cancer types. Such TAAs are useful as peptide vaccines against diseases associated with C1orf59 overexpression, e.g., cancer, more particularly, bladder cancer, breast cancer, cervical cancer, colorectal cancer, esophagus cancer, non-small cell lung cancer (NSCLC), osteosarcoma, ovarian cancer, pancreatic cancer, prostate cancer and small cell lung cancer (SCLC).

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated peptide selected from the group consisting of:
   (a) SEQ ID NO: 1, 3, 4, 7, 9, 13, 15, 17 or 20; and
   (b) SEQ ID NO: 1, 3, 4, 7, 9, 13, 15, 17 or 20 in which 1 or 2 amino acids are substituted as follows:
      (i) the second amino acid from the N-terminus is selected from the group of leucine and methionine; and/or
      (ii) the C-terminal amino acid is selected from the group of valine and leucine.

2. An isolated polynucleotide encoding a peptide of claim 1.

3. An agent for inducing CTL, wherein the agent comprises one or more peptides of claim 1 or one or more isolated polynucleotides encoding a peptide of claim 1.

4. An agent comprising one or more peptides of claim 1, or one or more isolated polynucleotides encoding a peptide of claim 1.

5. The agent of claim 4, which is formulated for the administration to a subject whose HLA antigen is HLA-A02.

6. A method for inducing an antigen-presenting cell (APC) with CTL inducibility, wherein the method comprises one of the following steps:
   (a) contacting an APC with a peptide of claim 1 in vitro, ex vivo or in vivo; and
   (b) introducing a polynucleotide encoding a peptide of claim 1 into an APC.

7. The isolated peptide of claim 1, which has CTL inducibility.

8. The isolated peptide of claim 1, which binds to an HLA antigen.

9. The isolated peptide of claim 8, wherein the HLA antigen is HLA-A02.

* * * * *

```
                         SEQUENCE LISTING

<160> NUMBER OF SEQ ID NOS: 47

<210> SEQ ID NO 1
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 1

Leu Gln Gln Glu Arg Phe Phe Lys Leu
1               5

<210> SEQ ID NO 2
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 2

Phe Cys Val Gly Asp Lys Phe Phe Val
1               5

<210> SEQ ID NO 3
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 3

Tyr Leu Ser Pro Ser Met Ile Val Ile
1               5

<210> SEQ ID NO 4
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 4

Arg Leu Leu Gly Phe Asp Leu Ile Thr
1               5

<210> SEQ ID NO 5
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 5

Leu Val Asn Glu Val Ser Gln Gln Val
1               5

<210> SEQ ID NO 6
<211> LENGTH: 9
<212> TYPE: PRT
```

```
<213> ORGANISM: Artificial
<220> FEATURE:
<223> OTHER INFORMATION: an artificially synthesized peptide sequence

<400> SEQUENCE: 6

Arg Leu Leu Lys Val Asn Pro Cys Ile
1               5

<210> SEQ ID NO 7
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 7

Leu Leu Gly Phe Asp Leu Ile Thr Cys
1               5

<210> SEQ ID NO 8
<211> LENGTH: 10
<212> TYPE: PRT
<213> ORGANISM: Homo sapiens

<400> SEQUENCE: 8

Leu Gln Gln Glu Arg Phe Phe Lys Leu Val
1               5                   10

<210> SEQ ID NO 9
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 9

Cys Leu Ser Glu Gln His Asp Gln His Val
1               5                   10

<210> SEQ ID NO 10
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 10

Ser Leu Gln Gln Glu Arg Phe Phe Lys Leu
1               5                   10

<210> SEQ ID NO 11
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 11

Val Leu Val Asn Glu Val Ser Gln Gln Val
1               5                   10

<210> SEQ ID NO 12
<211> LENGTH: 10
<212> TYPE: PRT
<213> ORGANISM: Artificial
<220> FEATURE:
<223> OTHER INFORMATION: an artificially synthesized peptide sequence
```

```
<400> SEQUENCE: 12

Leu Leu Ala Tyr Pro Lys Leu Asn Arg Leu
1               5                   10

<210> SEQ ID NO 13
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 13

Ser Leu Ala Pro Phe Leu Gly Asp Phe Leu
1               5                   10

<210> SEQ ID NO 14
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 14

Cys Val Gly Asp Lys Phe Phe Val Pro Leu
1               5                   10

<210> SEQ ID NO 15
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 15

Met Glu Phe Gln Thr Trp Ala Leu Tyr Val
1               5                   10

<210> SEQ ID NO 16
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 16

Arg Leu Leu Gly Phe Asp Leu Ile Thr Cys
1               5                   10

<210> SEQ ID NO 17
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 17

Leu Leu Gly Phe Asp Leu Ile Thr Cys Ile
1               5                   10

<210> SEQ ID NO 18
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 18
```

```
Pro Leu Tyr Arg Gln Arg Tyr Gln Phe Val
1               5                   10

<210> SEQ ID NO 19
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 19

Phe Glu Trp Thr Arg Met Glu Phe Gln Thr
1               5                   10

<210> SEQ ID NO 20
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 20

Tyr Val Ala Asn Arg Tyr Asp Tyr Ser Val
1               5                   10

<210> SEQ ID NO 21
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 21

Ser Val Val Asp Gly Asn Phe Glu Glu Val
1               5                   10

<210> SEQ ID NO 22
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 22

Lys Val Asn Pro Cys Ile Glu Leu Leu Val
1               5                   10

<210> SEQ ID NO 23
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 23

Ile Glu Asn Ser Pro Thr Pro Phe Cys Val
1               5                   10

<210> SEQ ID NO 24
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 24

Ala Val Phe Thr Thr Ser Tyr Pro Ser Leu
1               5                   10
```

```
<210> SEQ ID NO 25
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 25

Asn Tyr Phe Asp Glu Gln Phe Glu Phe
1               5

<210> SEQ ID NO 26
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 26

Gly Tyr Cys Thr Gln Ile Gly Ile Phe
1               5

<210> SEQ ID NO 27
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 27

Lys Phe Phe Val Pro Leu Gln Arg Leu
1               5

<210> SEQ ID NO 28
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 28

Phe Phe Val Pro Leu Gln Arg Leu Leu
1               5

<210> SEQ ID NO 29
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 29

Lys Phe Glu Trp Thr Arg Met Glu Phe
1               5

<210> SEQ ID NO 30
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 30

Arg Tyr Gln Phe Val Lys Asn Leu Val
1               5
```

```
<210> SEQ ID NO 31
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 31

Val Phe Thr Thr Ser Tyr Pro Ser Leu
1               5

<210> SEQ ID NO 32
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 32

Lys Val Asn Pro Cys Ile Glu Leu Leu
1               5

<210> SEQ ID NO 33
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 33

Phe Pro Glu Val Val Phe Gly Tyr Leu
1               5

<210> SEQ ID NO 34
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 34

Arg Tyr Asp Tyr Ser Val Glu Phe Thr
1               5

<210> SEQ ID NO 35
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 35

Ser Tyr Pro Ser Leu Gln Gln Glu Arg Phe
1               5                   10

<210> SEQ ID NO 36
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 36

Arg Phe Pro Glu Val Val Phe Gly Tyr Leu
1               5                   10

<210> SEQ ID NO 37
<211> LENGTH: 10
```

```
<212> TYPE: PRT
<213> ORGANISM: Artificial
<220> FEATURE:
<223> OTHER INFORMATION: an artificially synthesized peptide sequence

<400> SEQUENCE: 37

Gly Tyr Leu Phe Pro Ser Met Ile Val Ile
1               5                   10

<210> SEQ ID NO 38
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 38

Lys Phe Phe Val Pro Leu Gln Arg Leu Leu
1               5                   10

<210> SEQ ID NO 39
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 39

Asp Phe Leu Lys Pro Arg Asp Leu Asn Leu
1               5                   10

<210> SEQ ID NO 40
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 40

Gly Phe Asp Leu Ile Thr Cys Ile Glu Leu
1               5                   10

<210> SEQ ID NO 41
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 41

Arg Ser Val Ile Ala Asp Ser Ile Pro Leu
1               5                   10

<210> SEQ ID NO 42
<211> LENGTH: 1890
<212> TYPE: DNA
<213> ORGANISM: Homo sapiens

<400> SEQUENCE: 42
gtttttaggc ctttgccacg cctcgggagc gccacgaact caacagccgc ccaagccgcc      60
ttccggctcg cggtctgcgg acgcgctcgg agttgggggc cttcgccaac agctgccgta     120
ccgtgccgcg tcgcagccgc acgctagcgg ggtcaacggc gcggcaggcg cagggggtcct    180 cgccaaggtt cggaagagga ccttgaaaat ggcttctggg catgcgccac agcggccgtt     240
acgagacgca aaaccgacgc cttggaactg agagcctaga gggacggagc tcggcgcacc     300
```

```
atgaggctcc cggggcccaa ggccgaccgt gagagcgcac gagctgagtc agtgctgatt    360
ctctcaaata gagcttgaag gataaatctt cattttttgtt tcaacaaaac ttcgaaacaa   420
aatggaagaa ataatctac agtgcagtag tgtggttgac ggtaattttg aagaagttcc    480
cagggagacg gcaattcagt ttaaacctcc actatacaga cagcggtacc agttcgttaa    540
aaatttagtg gatcaacatg agcctaagaa ggttgcagac ctgggatgtg gtgatacttc    600
actcttaagg ctgctaaaag tcaatccatg cattgaattg cttgttggag tagatattaa    660
tgaggataaa ttacgatgga gaggggattc gttagctcct ttcctggggg attttctgaa    720
acctcgggat ctgaatttga ccatcacatt gtatcatggc tccgttgtgg agagagactc    780
tcgtttgctt ggatttgact tgataacgtg tattgaatta atagaacatt tggattcagg    840
tgatctggcc agatttcctg aagtggtatt tgggtacctg tctccatcca tgattgtcat    900
cagcacacca aactctgaat tcaatcccct gtttccatca gtgaccttaa agagattcaga   960
tcataaattt gagtggacca gaatggagtt tcagacctgg gctttatatg tggcaaatcg   1020
ctatgattac tctgtggagt ttactggtgt cggggaacca ccagctggag ctgagaatgt   1080
tggatactgt acccagatag gaatcttccg gaaaaatgga ggaaaggcaa cagaatcatg   1140
tctttcagag cagcatgatc agcatgttta taaagctgtt tttaccacct catacccaag   1200
cttacagcag gaaaggttct ttaaacttgt gttggttaat gaggtgtccc aacaagtgga   1260
aagcttaaga gtgagccacc tgccaaggcg gaaagaacag gctggggaac ggggtgataa   1320
gcccaaagac attggtggct caaaggcccc tgtcccatgc tttggaccag tcttcacaga   1380
ggttgagaag gccaagatag agaactctcc cacaccctc tgtgttggag ataaattttt   1440
cgtacctctg cagagactcc ttgcgtatcc caagttgaac cgcttatgtg ctaatgaaga   1500
gatgatgaga tcagtcattg ctgactcaat tcctctgagc agtgatggtt ctgcagtggt   1560
ggctgacctg cgtaattatt ttgatgaaca gtttgagttt tgaaccatgt ttatttcctg   1620
aaatttcagg gtctcagcga tagttgtgct cacttagaat ttagtttttt ttgtgtaatc   1680
ctaattcaag taatgttttt aaagtttcac tgcaaaagtc tatgttccaa gccattggac   1740
agacctgctt gagatatggc cagactgcag tgagccctga gaaagatatg agggtttaaa   1800
acgggtgctt tcctttgatt ttggactttt ttgttttctc aagaataaag aagttggatg   1860
tggtaatatg ttaattttga aaaaaaaaa                                      1890
```

<210> SEQ ID NO 43
<211> LENGTH: 393
<212> TYPE: PRT
<213> ORGANISM: Homo sapiens

<400> SEQUENCE: 43

```
Met Glu Glu Asn Asn Leu Gln Cys Ser Ser Val Val Asp Gly Asn Phe
1               5                   10                  15

Glu Glu Val Pro Arg Glu Thr Ala Ile Gln Phe Lys Pro Pro Leu Tyr
            20                  25                  30

Arg Gln Arg Tyr Gln Phe Val Lys Asn Leu Val Asp Gln His Glu Pro
        35                  40                  45

Lys Lys Val Ala Asp Leu Gly Cys Gly Asp Thr Ser Leu Leu Arg Leu
    50                  55                  60

Leu Lys Val Asn Pro Cys Ile Glu Leu Val Gly Val Asp Ile Asn
65                  70                  75                  80

Glu Asp Lys Leu Arg Trp Arg Gly Asp Ser Leu Ala Pro Phe Leu Gly
                85                  90                  95
```

-continued

Asp Phe Leu Lys Pro Arg Asp Leu Asn Leu Thr Ile Thr Leu Tyr His
            100                 105                 110

Gly Ser Val Val Glu Arg Asp Ser Arg Leu Leu Gly Phe Asp Leu Ile
        115                 120                 125

Thr Cys Ile Glu Leu Ile Glu His Leu Asp Ser Gly Asp Leu Ala Arg
    130                 135                 140

Phe Pro Glu Val Val Phe Gly Tyr Leu Ser Pro Ser Met Ile Val Ile
145                 150                 155                 160

Ser Thr Pro Asn Ser Glu Phe Asn Pro Leu Phe Pro Ser Val Thr Leu
                165                 170                 175

Arg Asp Ser Asp His Lys Phe Glu Trp Thr Arg Met Glu Phe Gln Thr
            180                 185                 190

Trp Ala Leu Tyr Val Ala Asn Arg Tyr Asp Tyr Ser Val Glu Phe Thr
        195                 200                 205

Gly Val Gly Glu Pro Pro Ala Gly Ala Glu Asn Val Gly Tyr Cys Thr
    210                 215                 220

Gln Ile Gly Ile Phe Arg Lys Asn Gly Gly Lys Ala Thr Glu Ser Cys
225                 230                 235                 240

Leu Ser Glu Gln His Asp Gln His Val Tyr Lys Ala Val Phe Thr Thr
                245                 250                 255

Ser Tyr Pro Ser Leu Gln Gln Glu Arg Phe Phe Lys Leu Val Leu Val
            260                 265                 270

Asn Glu Val Ser Gln Gln Val Glu Ser Leu Arg Val Ser His Leu Pro
        275                 280                 285

Arg Arg Lys Glu Gln Ala Gly Glu Arg Gly Asp Lys Pro Lys Asp Ile
    290                 295                 300

Gly Gly Ser Lys Ala Pro Val Pro Cys Phe Gly Pro Val Phe Thr Glu
305                 310                 315                 320

Val Glu Lys Ala Lys Ile Glu Asn Ser Pro Thr Pro Phe Cys Val Gly
                325                 330                 335

Asp Lys Phe Phe Val Pro Leu Gln Arg Leu Leu Ala Tyr Pro Lys Leu
            340                 345                 350

Asn Arg Leu Cys Ala Asn Glu Glu Met Met Arg Ser Val Ile Ala Asp
        355                 360                 365

Ser Ile Pro Leu Ser Ser Asp Gly Ser Ala Val Val Ala Asp Leu Arg
    370                 375                 380

Asn Tyr Phe Asp Glu Gln Phe Glu Phe
385                 390

<210> SEQ ID NO 44
<211> LENGTH: 22
<212> TYPE: DNA
<213> ORGANISM: Artificial
<220> FEATURE:
<223> OTHER INFORMATION: 5'-R primer

<400> SEQUENCE: 44
gtctaccagg cattcgcttc at                                          22

<210> SEQ ID NO 45
<211> LENGTH: 24
<212> TYPE: DNA
<213> ORGANISM: Artificial
<220> FEATURE:
<223> OTHER INFORMATION: 3-TRa-C

<400> SEQUENCE: 45
tcagctggac cacagccgca gcgt                                        24

```
<210> SEQ ID NO 46
<211> LENGTH: 21
<212> TYPE: DNA
<213> ORGANISM: Artificial
<220> FEATURE:
<223> OTHER INFORMATION: 3-TRbeta-C1

<400> SEQUENCE: 46
tcagaaatcc tttctcttga c                                              21

<210> SEQ ID NO 47
<211> LENGTH: 24
<212> TYPE: DNA
<213> ORGANISM: Artificial
<220> FEATURE:
<223> OTHER INFORMATION: 3-TRbeta-C2

<400> SEQUENCE: 47
ctagcctctg gaatcctttc tctt                                           24
```